(12) United States Patent
Chen et al.

(10) Patent No.: US 8,420,829 B2
(45) Date of Patent: Apr. 16, 2013

(54) PROCESSES FOR THE PREPARATION OF BENDAMUSTINE

(75) Inventors: Jian Chen, West Chester, PA (US); Katrin Przyuski, Phoenixville, PA (US); Renee Caroline Roemmele, Maple Glen, PA (US)

(73) Assignee: Cephalon, Inc., Frazer, PA (US)

( * ) Notice: Subject to any disclaimer, the term of this patent is extended or adjusted under 35 U.S.C. 154(b) by 0 days.

(21) Appl. No.: 13/079,888

(22) Filed: Apr. 5, 2011

(65) Prior Publication Data

US 2011/0190509 A1     Aug. 4, 2011

Related U.S. Application Data

(63) Continuation of application No. PCT/US2009/059765, filed on Oct. 7, 2009.

(60) Provisional application No. 61/103,696, filed on Oct. 8, 2008.

(51) Int. Cl.
*C07D 235/16*     (2006.01)

(52) U.S. Cl.
USPC ..................................................... 548/310.1

(58) Field of Classification Search ................. 548/310.1
See application file for complete search history.

(56) References Cited

FOREIGN PATENT DOCUMENTS

| DD | 34727 | 12/1964 |
|---|---|---|
| DD | 159877 | 4/1983 |
| DD | 293808 | 9/1991 |

OTHER PUBLICATIONS

Elderfield et al., Journal of Organic Chemistry (Nov. 1958), vol. 23, pp. 1749-1753.*
Jordan et al., Bioorganic & Medicinal Chemistry, vol. 10, (2002), pp. 2625-2633.*
An English translation of Gao et al., "Synthesis of Bendamustine Hydrochloride", Chinese Journal of New Drugs, 2007, vol. 16, No. 23, pp. 1960-1961.*
Carlson et al., Journal of Chemical Education, Feb. 2000, vol. 77, No. 2, pp. 270-271.*
An English translation of Ozegowski et al., "Omega-[bis(beta-chloroehtyl)aminobenzimidazol-2-yl]propionic or -butyric acids as potential cytostatics", Journal fuer Praktische Chemie, 1963, Series 4, vol. 20, pp. 178-186.*
Baumann, Journal of Chemical Education, Jan. 1979, vol. 56, Issue No. 1, p. 64.*
Hirschberg et al., Cancer Research, 1957, vol. 17, pp. 904-910.*
Ozegowski, Werner et al., "Omega-[bis(beta-chloroethyl) aminobenzimidazol-2-yl]-propionic or -butyric acids as potential cytostatics", Journal fuer Praktische Chemie, 1963, Series 4, vol. 20; 178-186.
Gao, Li-Mei et al., "Synthesis of Bendamustine Hydrochloride", Chinese Journal of New Drugs, 2007, vol. 16, No. 23, 1960-1961.
Delfourne, Evelyne et al., "Synthesis and in vitro antitumor activity of ring C and D-substituted phenanthrolin-7-one derivatives, analogues of the marine pyridoacridine alkaloids ascididemin and meridine", Bioorganic & Medicinal Chemistry, 2004, vol. 12, 3987-3994.
Palani, Anandan et al., "Biaryl ureas as potent and orally efficacious melanin concentrating hormone receptor 1 antagonists for the treatment of obesity", Journal of Medicinal Chemistry, 2005, 48(15), 4746-4749.
Marchini, Paolo et al., "Sodium borohydride-carboxylic acid systems, useful reagents for the alkylation of amines", J. Org. Chem., 1975, vol. 40, No. 23, 3453-3456.
Ozegowski et al., "IMET 3393, γ-[1-methyl-5-bis-(β-chloroethyl)-aminobenzimidazolyl-(2)]-butyric acid hydrochloride, a new cytostatic drug from the benzimidazole mustard gas series", *Zentralblatt fur die Pharmazie, Pharmakotherapie und Laboratoriumsdiagnostik—Journal of Abstracts and Reviews for Pharmacy, Pharmacotherapy, and Laboratory Diagnostics*] (1971), 110:10, pp. 1013-1019.
Sharpless et al., "A Greatly Improved Procedure for Ruthenium Tetraoxide Catalyzed Oxidations of Organic Compounds", *J. Org. Chem.* (1981), 46, pp. 3936-3938.
Delfourne et al., "Synthesis and In Vitro Antitumor Activity of Novel Ring D Analogues of the Marine Pyridoacridine Ascididemin: Structure—Activity Relationship", *J. Med. Chem.* (2002), 45, pp. 3765-3771.

* cited by examiner

*Primary Examiner* — Laura L. Stockton

(57) ABSTRACT

New methods for the preparation of bendamustine, and the pharmaceutical salts thereof, are described. Novel compounds useful for the preparation of bendamustine are also described.

35 Claims, 5 Drawing Sheets

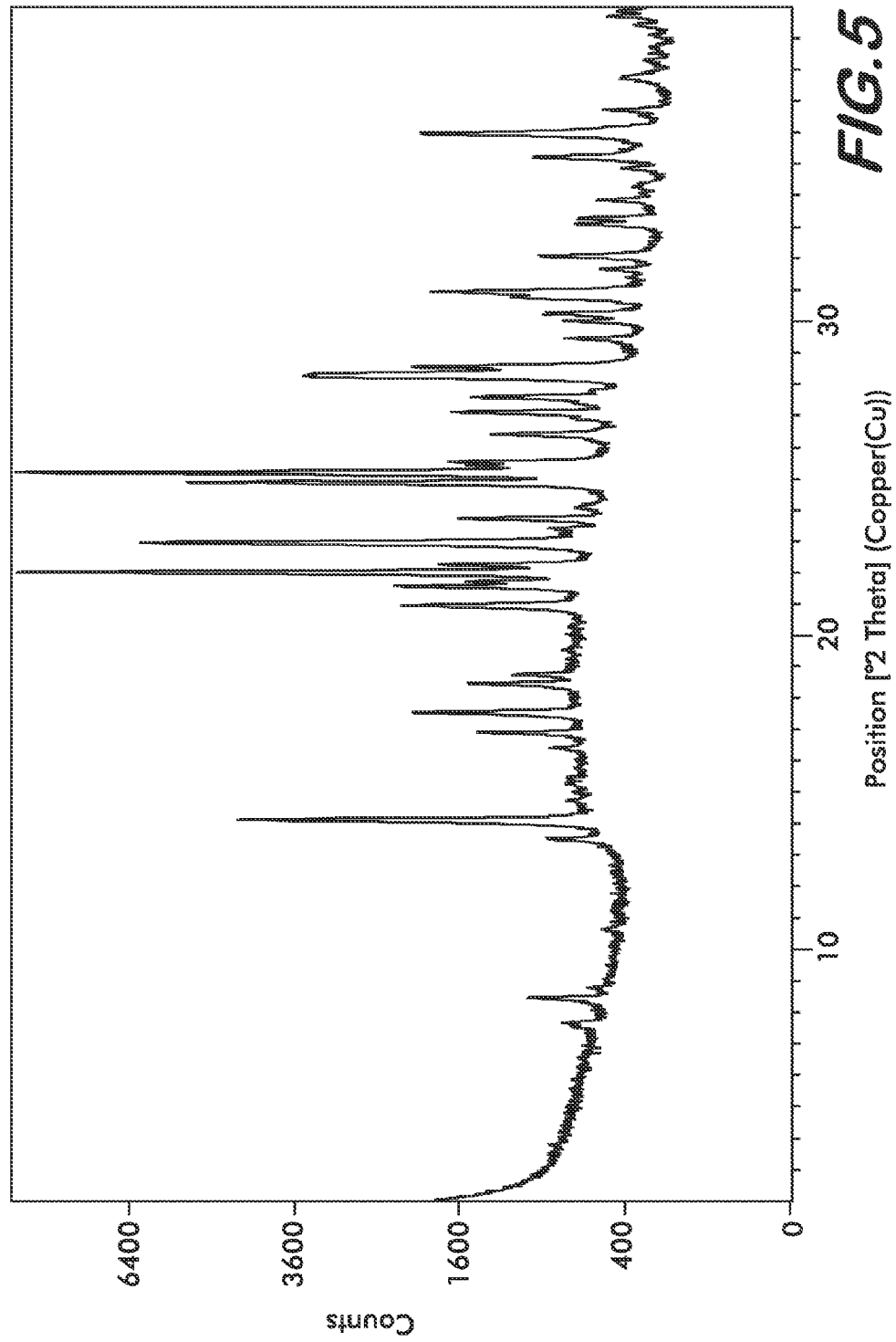

PROCESSES FOR THE PREPARATION OF BENDAMUSTINE

FIELD OF THE INVENTION

The invention relates to improved methods for the synthesis of bendamustine, in particular, bendamustine hydrochloride.

BACKGROUND OF THE INVENTION

Bendamustine hydrochloride, 4-{5-[bis(2-chloroethyl)amino]-1-methyl-2-benzimidazolyl}butyric acid hydrochloride salt:

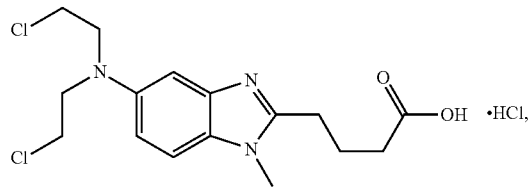

Bendamustine Hydrochloride was initially synthesized in 1963 in the German Democratic Republic (GDR) and was available from 1971 to 1992 there under the tradename Cytostasan®. Since that time, it has been marketed in Germany under the tradename Ribomustin®. Bendamustine hydrochloride is currently available in the United States under the tradename Treanda®(Cephalon, Inc., Frazer, Pa.). Bendamustine is an alkylating agent that has been shown to have therapeutic utility in treating diseases such as chronic lymphocytic leukemia, Hodgkin's disease, non-Hodgkin's lymphoma, multiple myeloma, and breast cancer.

The current commercial preparation of bendamustine hydrochloride entails at least nine synthetic steps, involving the use of several hazardous, odiferous reagents, such as thionyl chloride. See, for example, *J. Prakt. Chem.* 20, 178-186 (1963) and *Zentralblatt fuer Pharmazie, Pharmakotherapie und Laboratoriumsdiagnostik* 110 (10), 1013-1019 (1971). Despite its longstanding use in Germany, there have been very few attempts to modify the synthesis of bendamustine in order to reduce the number of synthetic steps and personnel exposure to hazardous reagents. As such, a need exists for a new synthesis of bendamustine that requires fewer synthetic steps and employs fewer hazardous reagents.

SUMMARY OF THE INVENTION

The present invention is directed to improved methods for the preparation of bendamustine, and the pharmaceutically acceptable salts thereof. Some embodiments comprise contacting 1-methylamino-2,4-dinitrobenzene:

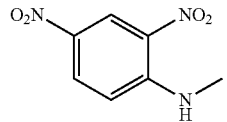

with a compound of formula V:

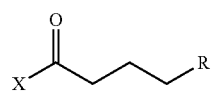

wherein X is Cl, Br, or I and R is a masked carboxylic acid; for a time and under conditions sufficient to produce a compound of formula III:

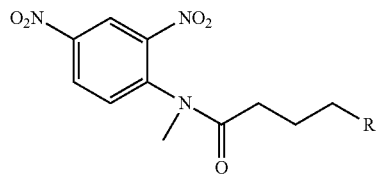

Other embodiments comprise contacting 2,4-dinitroaniline:

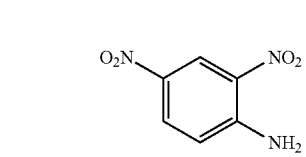 [SMILES: Nc1ccc([N+](=O)[O-])cc1[N+](=O)[O-]]

with a compound of formula V:

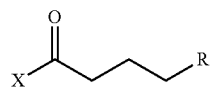

wherein X is Cl, Br, or I and R is a masked carboxylic acid; for a time and under conditions sufficient to produce the compound of formula VI:

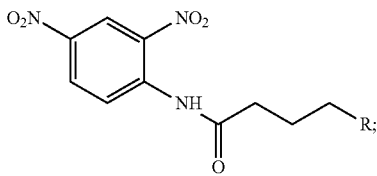

optionally isolating the compound of formula VI; and methylating the compound of formula VI for a time and under conditions sufficient to produce a compound of formula III:

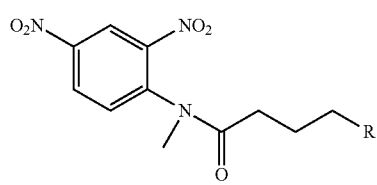

Other embodiments comprise contacting 2,4-dinitroaniline:

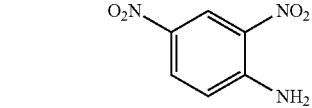

with a compound of formula V:

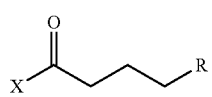

wherein X is OH and R is a masked carboxylic acid;
for a time and under conditions sufficient to produce a compound of formula VI:

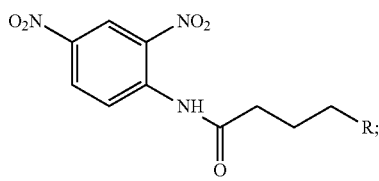

optionally isolating the compound of formula VI; and
methylating the compound of formula VI for a time and under conditions sufficient to produce a compound of formula III:

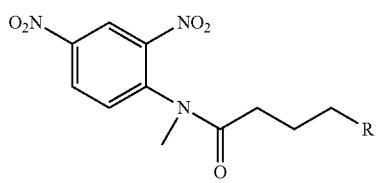

The invention further includes reducing the compound of formula III for a time and under conditions sufficient to reduce the nitro groups and form a compound of formula IV:

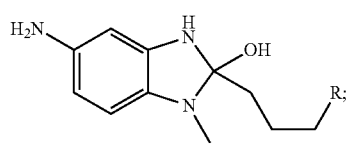

dehydrating the compound of formula IV for a time and under conditions sufficient to produce a compound of formula II:

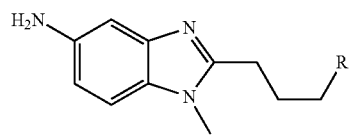

optionally isolating the compound of formula II;
reductively alkylating the compound of formula II to produce a compound of formula I:

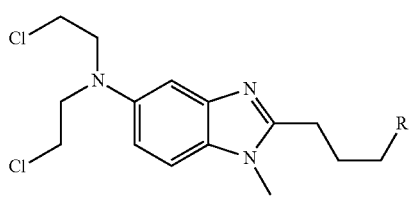

treating the compound of formula I, for a time and under conditions sufficient to form bendamustine, or a pharmaceutically acceptable salt thereof; isolating bendamustine or the pharmaceutically acceptable salt thereof; and optionally purifying bendamustine, or the pharmaceutically acceptable salt thereof. A preferred embodiment of the invention encompasses hydrolyzing the compound of formula I, where R is a masked carboxylic acid capable of formation of a carboxylic acid under hydrolysis conditions, for a time and under conditions sufficient to form bendamustine, or a pharmaceutically acceptable salt thereof; isolating bendamustine or the pharmaceutically acceptable salt thereof; and optionally purifying bendamustine, or the pharmaceutically acceptable salt thereof. Bendamustine, and the pharmaceutically acceptable salts thereof, produced by the processes of the claimed invention are also described.

BRIEF DESCRIPTION OF THE DRAWINGS

FIG. 5 is an XRPD spectrum of bendamustine hydrochloride purified by Method 5 described herein.

DETAILED DESCRIPTION OF THE INVENTION

Figure 1:
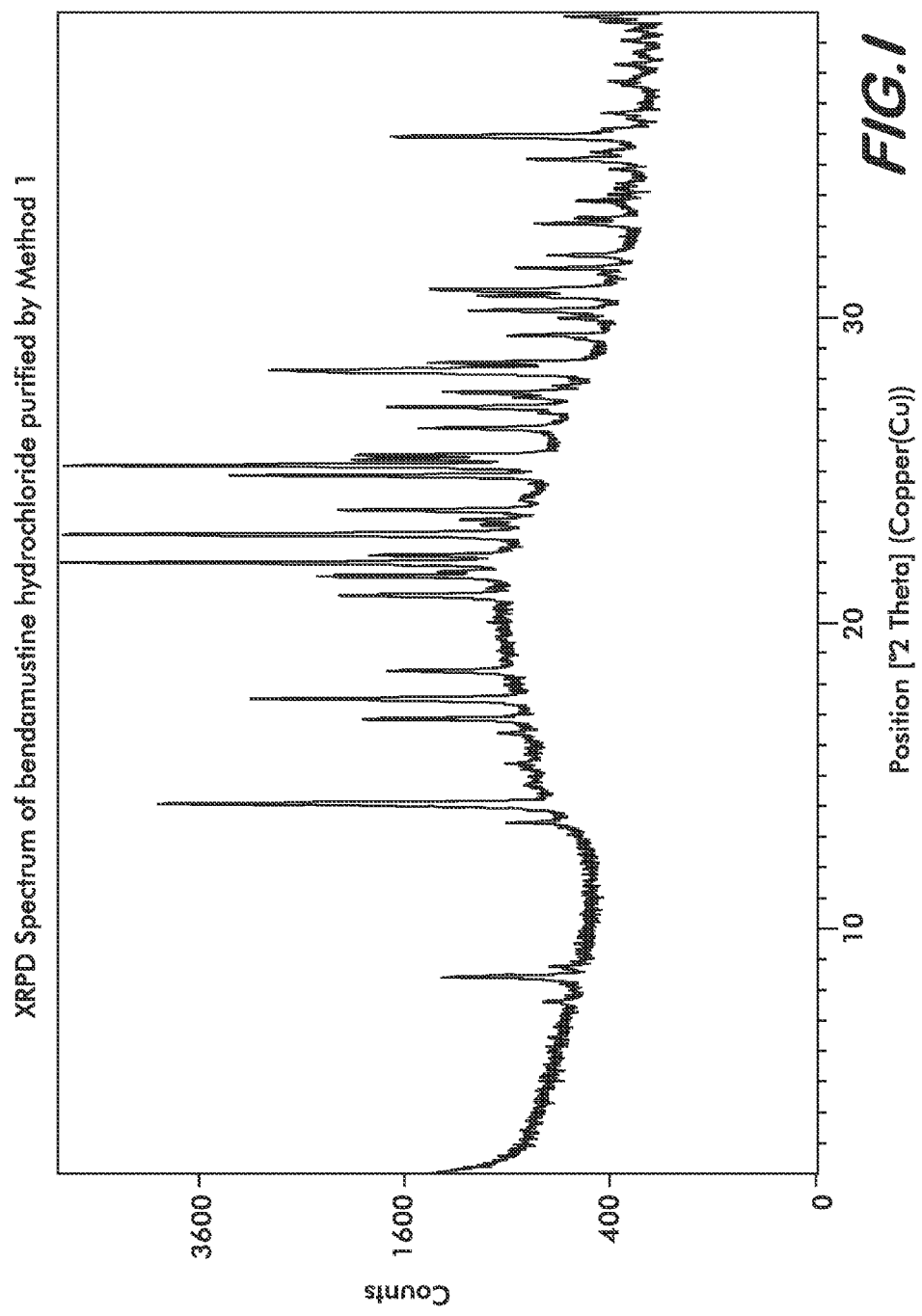
FIG. 1 is an XRPD spectrum of bendamustine hydrochloride purified by Method 1 described herein.

New methods for the synthesis of bendamustine, in particular, pharmaceutically acceptable salts of bendamustine such as bendamustine hydrochloride, have been developed and are disclosed herein. In certain embodiments, bendamustine can be prepared in six steps from commercially available starting materials. Notably, the chloroethyl side chains of bendamustine are introduced in a single, reductive alkylation step, compared to prior art methods that require at least two steps to introduce the chloroethyl groups. The methods also include a novel preparation of the unsymmetrical benzimidazole precursor of bendamustine. Further details regarding these methods are described below and in the accompanying Schemes.

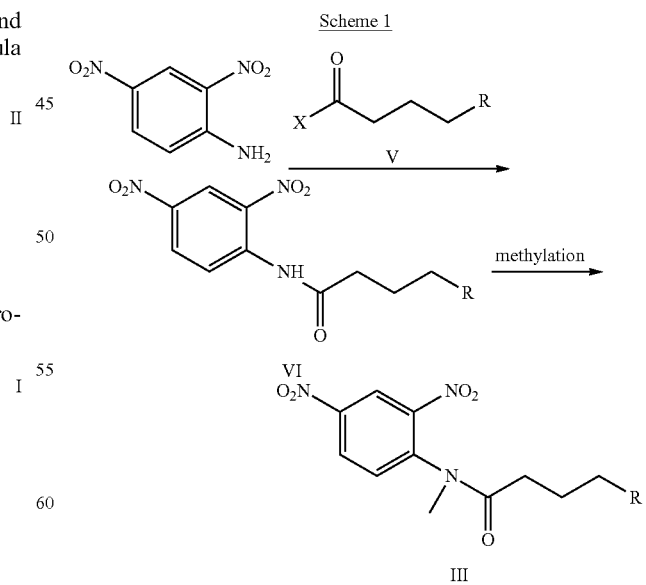

X = Cl, Br, I
R = masked carboxylic acid

An exemplary method for the preparation of pharmaceutically acceptable salts of bendamustine begins with 2,4-dinitroaniline, as shown in Scheme 1. 2,4-Dinitroaniline is converted to a compound of formula VI, wherein R is a masked carboxylic acid.

As used herein, the term "masked carboxylic acid" refers to any chemical moiety that can be converted to a carboxylic acid (—COOH) functional group through one or more chemical transformations. Examples of masked carboxylic acids include, for example, esters, thioesters, oxazoles, nitriles, amides, alkyl alcohols, phenyls, ethers, and orthoesters. In preferred embodiments of the present invention, R is a masked carboxylic acid that is —C(=O)OC$_{1-6}$alkyl, —C(=O)Ophenyl, —C(=O)SC$_{1-6}$alkyl, -oxazole, —CN, —C(=O)NH$_2$, —C(=O)NH(R$_1$), —C(=O)N(R$_1$)$_2$, —CH$_2$OH, -phenyl, —CH$_2$OC$_{1-6}$alkyl, or —C(OC$_{1-6}$alkyl)$_3$, wherein each R$_1$ is independently, for example, alkyl, cycloalkyl, or aryl.

2,4-Dinitroaniline is converted to a compound of formula VI, wherein R is a masked carboxylic acid, by treatment with a compound of formula V, wherein R is a masked carboxylic acid, preferably, in the compound of formula V, R is —C(=O)OC$_{1-6}$alkyl, —C(=O)Ophenyl, —C(=O)SC$_{1-6}$alkyl, -oxazole, —CN, —C(=O)NH(C$_{1-6}$alkyl), —C(=O)N(C$_{1-6}$alkyl)$_2$, -phenyl, —CH$_2$OC$_{1-6}$alkyl, or —C(OC$_{1-6}$alkyl)$_3$ and X is chloro, bromo, or iodo (Cl, Br, or I). Preferably, R is —C(=O)OCH$_3$ or —C(=O)OCH$_2$CH$_3$, most preferably —C(=O)OCH$_3$. In exemplary embodiments, X is chloro. In particularly preferred embodiments, the compound of formula V is methyl-5-chloro-5-oxo-valerate. Exemplary conditions for converting phenyl to carboxylic acid can be found in, for example, Sharpless, et al., *J. Org. Chem.* 1981, 46, 3936-3938.

The preparation of the compound of formula VI from 2,4-dinitroaniline is typically carried out in the presence of an organic solvent. The reaction is also typically carried out at a temperature that is greater than ambient temperature, preferably at least about 50° C., most preferably, the reaction temperature is greater than about 75° C. or greater than about 100° C. In some embodiments, the reaction is carried out at the boiling point of the organic solvent. Preferred organic solvents include acetonitrile and toluene.

In other embodiments, the compound of formula V is combined with 2,4-dinitroaniline in the presence of base, for example, an inorganic base such as potassium carbonate or an amine base such as triethylamine. Preferred organic solvents for such embodiments include dimethylacetamide, ethyl acetate, dichloromethane, toluene, or a mixture thereof. Preferably, the reactions are carried out at ambient temperature or higher, for example, about 50° C.

In still other embodiments, 2,4-dinitroaniline can be converted to a compound of formula VI via the coupling of the aniline with a suitable carboxylic acid, for example, HOOC—(CH$_2$)$_3$R, wherein R is a masked carboxylic acid, for example, wherein R is —C(=O)OC$_{1-6}$alkyl, —C(=O)Ophenyl, —C(=O)SC$_{1-6}$alkyl, -oxazole, —CN, —C(=O)NH$_2$, —C(=O)NH(C$_{1-6}$alkyl), —C(=O)N(C$_{1-6}$alkyl)$_2$, —CH$_2$OH, -phenyl, —CH$_2$OC$_{1-6}$alkyl, or —C(OC$_{1-6}$alkyl)$_3$. Preferably, the carboxylic acid is pentanedioic acid monomethylester. Such couplings are well known in the art and can be accomplished using known coupling reagents. For example, 1-ethyl-3-(3'-dimethylaminopropyl)carbodiimide (EDCI) with catalytic dimethylaminopyridine (DMAP). Couplings are typically carried out in the presence of an organic solvent, for example, dichloromethane or toluene, at temperatures ranging from 0° C. to ambient temperature to the boiling point of the organic solvent, i.e., reflux. In an alternative embodiment, 2,4-dinitroaniline can be coupled with an appropriate carboxylic acid in the presence of boric acid in a solvent such as toluene at elevated temperature, for example, reflux.

The compound of formula VI can be isolated, if desired, and treated with a methylating agent and base, preferably an inorganic base, to provide the compound of formula III. Preferred methylating agents include methyl iodide and dimethyl sulfate. One exemplary base is potassium carbonate. Other bases include sodium bicarbonate, sodium carbonate, potassium bicarbonate, cesium carbonate, cesium bicarbonate, and rubidium carbonate. Typically, the methylation is carried out in an organic solvent, for example, acetonitrile.

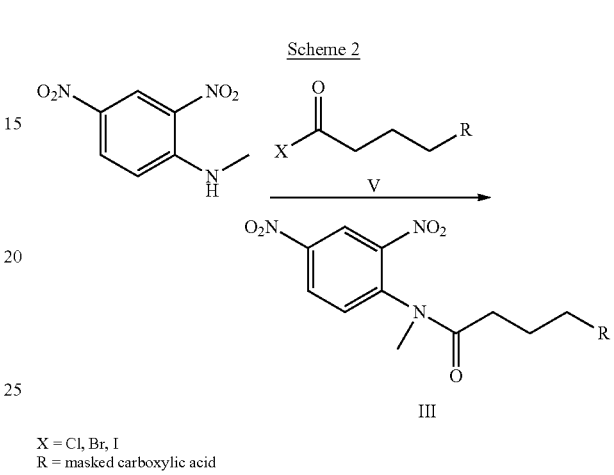

Scheme 2

X = Cl, Br, I
R = masked carboxylic acid

An alternate embodiment for the preparation of a compound of formula III is shown in Scheme 2. Treatment of 1-methylamino-2,4-dinitrobenzene with a compound of formula V, wherein X is Cl, Br, or I, preferably Cl, and R is —C(=O)OC$_{1-6}$alkyl, —C(=O)Ophenyl, —C(=O)SC$_{1-6}$alkyl, -oxazole, —CN, —C(=O)NH(C$_{1-6}$alkyl), —C(=O)N(C$_{1-6}$alkyl)$_2$, -phenyl, —CH$_2$OC$_{1-6}$alkyl, or —C(OC$_{1-6}$alkyl)$_3$, preferably —C(=O)OCH$_3$ or —C(=O)OCH$_2$CH$_3$, most preferably —C(=O)OCH$_3$, will produce the compound of formula III. This reaction is generally carried out in the presence of an organic solvent, for example, xylene or a mixture of xylenes. The reaction is typically carried out above ambient temperature, for example, at reflux.

In other embodiments, 1-methylamino-2,4-dinitrobenzene can be converted to a compound of formula III by treatment with a compound of formula V in the presence of a base, for example, sodium, lithium, or potassium hexamethyldisilazane, lithium diisopropyl amide, butyllithium, sodium hydride, or potassium t-butoxide. Preferably, the reaction is carried out in an organic solvent, for example, dimethylacetamide, tetrahydrofuran, dimethylsulfoxide, or a mixture thereof. The reaction temperature is typically in a lower range of from about −65° C. to about −20° C. to about 0° C. to a higher range of ambient temperature to about 50° C.

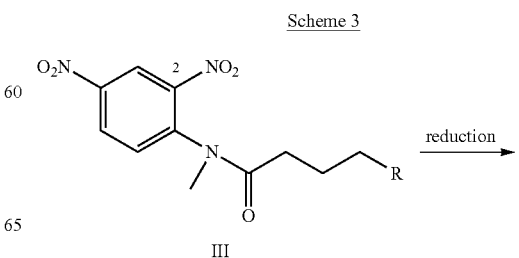

Scheme 3

-continued

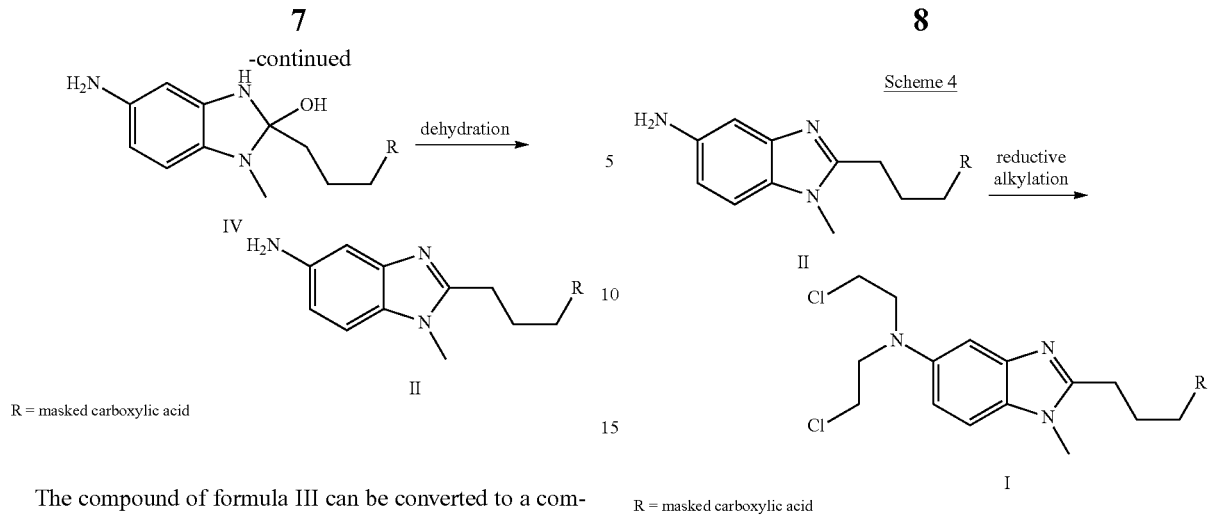

R = masked carboxylic acid

The compound of formula III can be converted to a compound of formula II via the method shown in Scheme 3. The nitro groups of the compound of formula III can be reduced to the corresponding amines using reduction techniques known in the art. Preferably, the reduction is via catalytic hydrogenation. An exemplary catalyst for the catalytic hydrogenation is palladium, preferably, palladium on carbon (for instance, 5% palladium or 10% palladium) or palladium hydroxide (about 20% palladium). Typically, the catalytic hydrogenation is carried out under a pressure of hydrogen that is greater than atmospheric pressure. A preferred pressure of hydrogen is about 20 psi to about 100 psi, preferably at least 40 psi. The hydrogenation is typically carried out in the presence of a $C_{1-6}$alkyl alcohol, for example ethanol or methanol, with methanol being particularly preferred. Tetrahydrofuran and water are also a suitable solvents. In preferred embodiments, the hydrogenation is carried out at ambient temperature to about 60° C.

In other embodiments, the reduction may be carried out by employing a reagent such as sodium dithionite with an acid such as acetic acid. Such embodiments are typically carried out in aqueous solution at ambient temperature.

Reduction of the C(2) (see Scheme 3) nitro generally results in in situ cyclization to form the compound of formula IV. The compound of formula IV may optionally be isolated. After optional removal of any catalyst, preferably by filtration, the reaction mixture (or filtrate, if filtration employed) is treated with acid, preferably concentrated acid, to dehydrate the compound of formula IV to produce the compound of formula II. Preferably, concentrated hydrochloric acid is used to dehydrate, resulting in the hydrochloric acid salt of the compound of formula II being generated. Other acids, such as sulfuric acid, hydrobromic acid, and phosphoric acid, would also be acceptable acids and would form the corresponding salts. Preferred solvents include alcohols, for example methanol and ethanol, and tetrahydrofuran. Mixtures of solvents may also be employed. Typically, the reaction is carried out at the boiling point of the solvent system used. The compound of formula II may be precipitated from the reaction mixture by addition of an appropriate anti-solvent, for example tetrahydrofuran or methyl t-butyl ether. This step may optionally be carried out by the addition of the acid during the nitro reduction step. Typically, this step is carried out at a temperature above ambient temperature.

In other embodiments, the dehydration can be carried out in the presence of base, for example, sodium hydroxide. In other embodiments, the dehydration can be accomplished by the application of heat.

Scheme 4

R = masked carboxylic acid

The novel reductive alkylation of the compound of formula II, either the salt or the free base, preferably in the presence of chloroacetic acid produces the compound of formula I, as shown in Scheme 4. In exemplary embodiments, chloroacetic acid is used and the reducing agent is borane, preferably borane-tetrahydrofuran, lithium borohydride, or sodium borohydride. The reaction is generally carried out in the presence of an organic solvent, for example tetrahydrofuran, at temperatures at or above ambient temperature, for example, ambient temperature to about 90° C., preferably at about 40-60° C.

In other embodiments, chloroacetaldehyde is used with suitable reducing agents including borane sodium cyanoborohydride (optionally in the presence of phosphate buffer), sodium triacetoxyborohydride, and sodium borohydride (e.g., sodium borohydride or sodium borohydride in solution, for example diglyme or aqueous sodium hydroxide solution) or lithium borohydride and solutions thereof. Preferred solvents for carrying out the reaction include methanol, dichloromethane, water, acetonitrile, dichloroethane, dimethylacetamide, tetrahydrofuran, toluene, or a mixture thereof. The reaction is typically carried out at ambient temperature or from about 0° C. to about 60° C. See Palani, A., et al. J. Med. Chem. 2005, 48, 4746; Delfourne, E., Bioor. & Med. Chem. 2004, 12, 3987; Delfourne, E., et al. J. Med. Chem. 2002, 45, 3765.

Reduction via hydrogenation is also suitable. Preferred hydrogenation conditions include catalytic hydrogenation, using, for example palladium on carbon as the catalyst. Hydrogen may be added as $H_2$ gas at pressures ranging from atmospheric pressure to about 145 psi. In situ hydrogen generation may also be employed. The hydrogenation is typically carried out at ambient temperature. Ammonium bicarbonate and palladium on carbon is also suitable.

Scheme 5

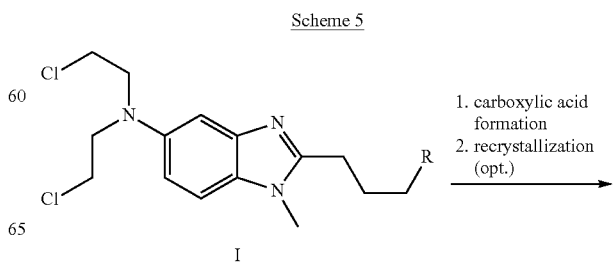

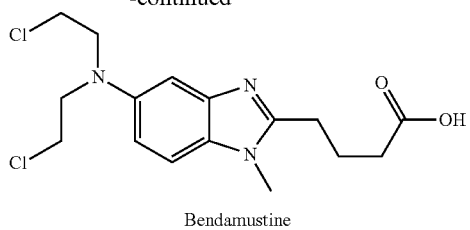

Bendamustine

R = masked carboxylic acid

Preparation of Bendamustine from the Compound of Formula I can be Performed according to the procedure set forth in Scheme 5. The masked carboxylic acid group (R) is converted to the corresponding carboxylic acid using methods known to those skilled n the art. In preferred embodiments, where the masked carboxylic acid is capable of formation of a carboxylic acid under hydrolysis conditions, the masked carboxylic acid of the compound of formula I is hydrolyzed to produce bendamustine, or preferably the salt thereof. Embodiments containing masked carboxylic acids so capable include those wherein R is —C(=O)OC$_{1-6}$alkyl, —C(=O)Ophenyl, —C(=O)SC$_{1-6}$alkyl, -oxazole, —CN, —C(=O)NH$_2$, —C(=O)NH(C$_{1-6}$alkyl), —C(=O)N(C$_{1-6}$alkyl)$_2$, or —C(OC$_{1-6}$alkyl)$_3$. In some embodiments, R is —C(=O)OC$_{1-6}$alkyl that is converted to the carboxylic acid via hydrolysis. Preferably, acid is used for the hydrolysis and is preferably concentrated hydrochloric acid, which produces the hydrochloric acid salt of bendamustine. Generally, the hydrolysis is carried out at ambient temperature or above, for example, ambient temperature to reflux, preferably at about 80° C. to about 100° C. Preferably, where the salt produced is the hydrochloride salt, the salt may be recrystallized.

Alternatively, hydrolysis of the compound of formula I can be accomplished with a hydroxide, for example lithium hydroxide, in a solvent mixture containing water, such as methanol and water. The reaction is typically carried out at below room temperature, for example, at between about 0° C. to about 12° C.

In another embodiment, bendamustine can be prepared directly from the compound of formula II. In such embodiments, when the reductive alkylation is completed, as observed by, for example, HPLC, about one half to three-quarters of the solvent volume is removed in vacuo. Concentrated acid, for example hydrochloric acid, or any other suitable acid, is then added. The reaction is typically heated to reflux to produce bendamustine, or a pharmaceutically acceptable salt thereof.

Bendamustine, or the pharmaceutically acceptable salt thereof, prepared according to the methods of the present invention, when analyzed by any known analytical method, for example, HPLC, gas chromatography, or NMR, will preferably have a bendamustine purity of at least about 85%. In the most preferred embodiments, the methods will produce bendamustine having a purity of at least about 90%. More preferably, the methods will produce bendamustine having a purity of at least about 95%. Most preferable, the methods will produce bendamustine having a purity of at least about 98%.

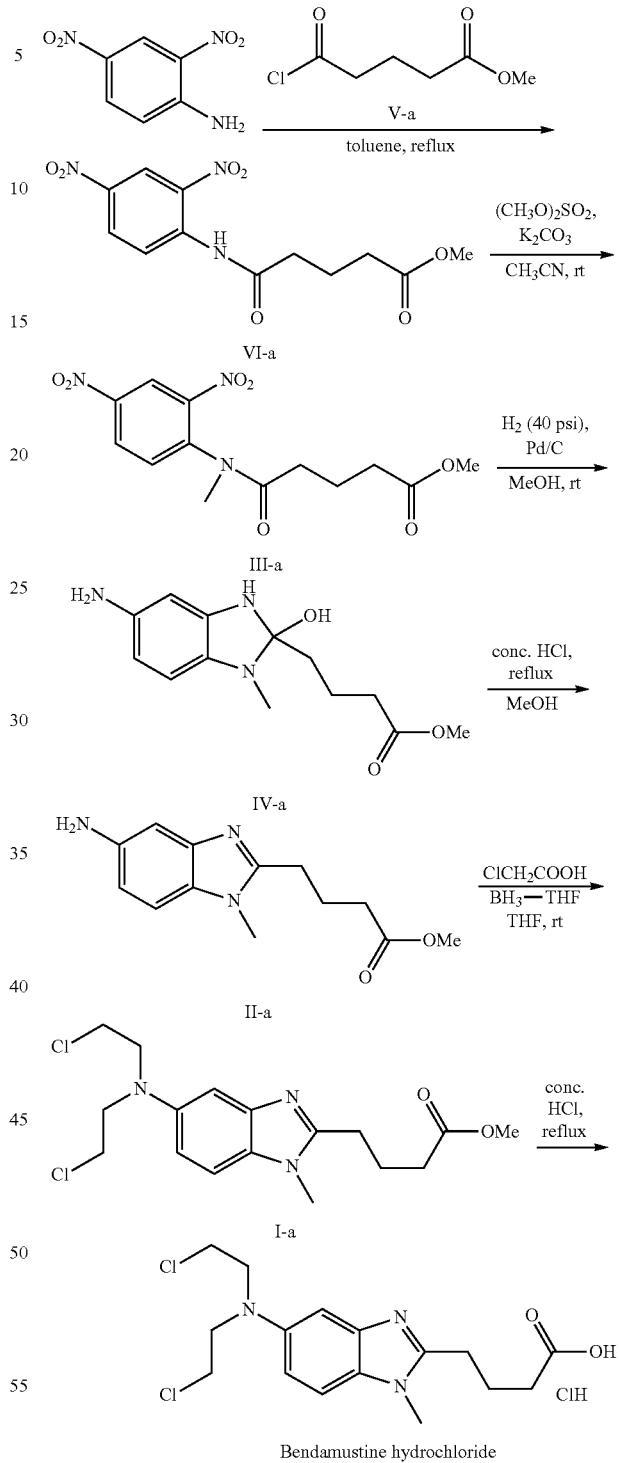

Scheme 6

Bendamustine hydrochloride

A preferred preparation of bendamustine hydrochloride, using the methods described herein, is depicted in Scheme 6. 2,4-dinitroaniline was reacted with methyl-5-chloro-5-oxo-valerate (V-a) in toluene at reflux to produce the compound of formula VI-a. Methylation of VI-a with dimethylsulfate in acetonitrile at ambient temperature, using potassium carbonate as the base, produced the compound of formula III-a. In certain embodiments, methyl iodide can be used in place of the dimethylsulfate. Catalytic hydrogenation of III-a, using palladium on carbon and about 40 psi of hydrogen, at ambient temperature, using methanol as solvent, produced the compound of formula IV-a. Acid-mediated dehydration using concentrated hydrochloric acid at reflux produced the compound of formula II-a. Reductive alkylation of II-a, using borane-tetrahydrofuran and chloroacetic acid at ambient temperature, produced the compound of formula I-a. Acid-mediated hydrolysis using concentrated hydrochloric acid at reflux produced bendamustine hydrochloride.

Scheme 7

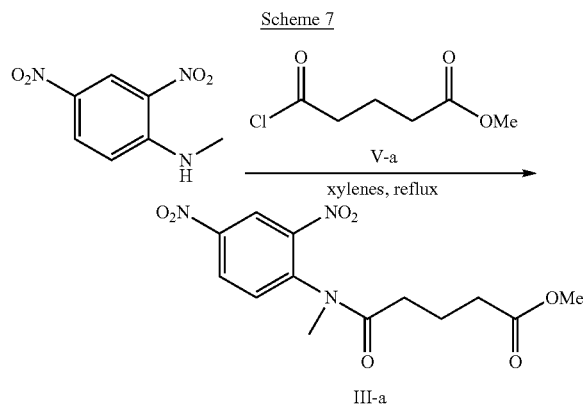

The compound of formula III-a can alternatively be prepared according to the scheme shown in Scheme 7. Reaction of 1-methylamino-2,4-dinitrobenzene with methyl-5-chloro-5-oxo-valerate in xylenes at reflux produced the compound of formula III-a. Compound III-a can then be transformed into bendamustine hydrochloride using the reaction sequence set forth in Scheme 6.

The following examples are meant to be illustrative, not limiting, of the methods of the present invention.

EXAMPLES

High Performance Liquid Chromatography (HPLC) methods referred to in the following Examples were performed as follows:

HPLC Method A:

| Column: | Agilent Zorbax XDB-C18, 4.6 × 150 mm |
|---|---|
| Flow Rate: | 1.0 ml/min |
| Solvent A: | 0.1% Trifluoroacetic acid in water |
| Solvent B: | 0.1% Trifluoroacetic acid in acetonitrile |
| Wavelength: | 254 nm |

| Timetable: | Time | % Solvent B |
|---|---|---|
| | 0 | 10 |
| | 10 | 90 |
| | 15 | 90 |

| Stop Time: | 16 minutes |
|---|---|
| Post Time | 5 minutes |

HPLC Method B:

| Column: | Waters X-Terra MS C-18 3.5 µm, 4.6 × 150 mm |
|---|---|
| Flow Rate: | 1.0 ml/min |
| Solvent A: | 10 mM aqueous ammonium bicarbonate, pH = 9 |
| Solvent B: | Acetonitrile |
| Wavelength: | 220 and 254 nm |

| Timetable: | Time | % Solvent B |
|---|---|---|
| | 0.00 | 0 |
| | 15.00 | 90 |
| | 17.00 | 90 |
| | 17.01 | 0 |
| | 19.00 | 0 |

| Stop Time: | 19 minutes |
|---|---|
| Post Time | 3 minutes |

HPLC Method C:

| Column: | Zorbax Bonus-RP, 5 µm, 4.6 × 150 mm |
|---|---|
| Flow Rate: | 1.0 ml/min |
| Solvent A: | 0.1% Trifluoroacetic acid in water |
| Solvent B: | 0.1% Trifluoroacetic acid in acetonitrile |
| Wavelength: | 254 nm |

| Timetable: | Time | % Solvent B |
|---|---|---|
| | 0.00 | 7.0 |
| | 5.00 | 7.0 |
| | 13.00 | 27.0 |
| | 16.00 | 27.0 |
| | 25.00 | 57.0 |
| | 26.00 | 90.0 |
| | 31.00 | 90.0 |
| | 31.01 | 7.0 |

| Stop Time: | 30.01 minutes |
|---|---|
| Post Time | 5 minutes |

Example 1

Preparation of 4-(2,4-Dinitro-phenylcarbamoyl)-butyric acid methyl ester: To a 250 mL round bottom 3-neck flask equipped with a stir bar, heating mantle, reflux condenser, thermocouple, and $N_2$ sweep were charged 10.0 g (54.6 mmol) of 2,4-dinitroaniline and 100 mL (10 volumes) of toluene at room temperature. To this stirred mixture was added 9.06 mL (10.78 g, 65.5 mmol, 1.2 equiv) of methyl-5-chloro-5-oxo-valerate via syringe. This yellow reaction mixture was then heated to reflux at 110° C. Dissolution occurred at about 100° C. Reaction progress was periodically monitored by High Performance Liquid Chromatography, HPLC Method A. The reaction was complete after 18.5 hours at reflux and was cooled to 50° C.

The approximately 100 mL of reaction mixture was then added to 100 mL of water in a round bottom flask and the toluene was removed in vacuo. The desired product precipitated as yellow solids and the resultant product slurry was stirred at room temperature for 1 hour. The solids were then isolated by vacuum filtration and dried overnight at 60° C., yielding 16.67 g (98%, 53.6 mmol, 99.0 HPLC Area % (HPLC Method A)). $^1$H NMR (400 MHz, $CDCl_3$) δ 10.7 (s, b, 1H), 9.14 (d, J=2.68 Hz, 1H), 9.10 (d, J=9.44 Hz, 1H), 8.5 (dd, 1H), 3.7 (s, 3H), 2.65 (t, J=7.32 Hz, 2H), 2.48 (t, J=7.08 Hz, 2H), 2.10 (m, 2H).

Example 1a

Preparation of 4-(2,4-Dinitro-phenylcarbamoyl)-butyric acid methyl ester: The reactor is cleaned and dried then charged with 2,4-dinitroaniline, the limiting reagent at room temperature (15-25° C.). The reactor is inerted and 10 volumes of toluene are charged. Agitation is begun to suspend the solids and 1.2 equivalents of methyl glutaryl chloride is charged. The batch is slowly heated to reflux. Solids dissolve between 80-90° C. Throughout the heating, hydrogen chloride gas is evolved and must be scrubbed. Once at reflux the batch is held for 4-6 hours until an in process analysis shows less than 1.0 Area % 2,4-dinitroaniline remaining (HPLC Method A). The batch is cooled to 55±5° C. and washed with 6 volumes of 1:1 saturated sodium bicarbonate/brine. After the layers are separated a vacuum distillation is carried out to remove one-third of the initial toluene charge. At greater than 50° C. this same volume of heptane is charged as an antisolvent. The batch is then cooled to 45° C. and seeded with 0.1 to 1.0 wt % 4-(2,4-dinitro-phenylcarbamoyl)-butyric acid methyl ester, and aged for three hours before being cooled to 5° C. with the following profile: 2° C./hour to 35° C., 6° C./hour to 20° C., 15° C./hour to 5° C. then held at 5° C. for 1 hour. The solids are then collected by vacuum filtration, washed with 1 volume of 2:1 toluene/heptane at 5° C., then dried in a vacuum oven at 50° C. to constant weight. The yield is typically 85-95% and purity ranges from 98-99 Area % by HPLC Method A.

Example 2

Preparation of 4-[(2,4-Dinitro-phenyl)-methyl-carbamoyl]-butyric acid methyl ester: To a 100 mL round bottom 3-neck flask equipped with stir bar, thermocouple, and $N_2$ sweep were charged 16.67 g (53.6 mmol) of 4-(2,4-dinitro-phenylcarbamoyl)-butyric acid methyl ester and 50 mL (5 volumes vs. dinitroaniline) of acetonitrile at room temperature. To this clear yellow stirred solution was then added 6.09 mL (8.10 g, 64.2 mmol, 1.2 equiv) of dimethyl sulfate and 14.80 g (107 mmol, 2.0 equiv) of $K_2CO_3$. The mixture turned dark reddish orange with the addition and exhibited an exotherm of less than 5° C. The reaction was monitored periodically by HPLC Method A and was complete after 22.5 hours at room temperature.

The reaction mixture was filtered to remove the $K_2CO_3$ and the wetcake was washed with acetonitrile. The resultant 60 mL of dark purple filtrate was then added dropwise via an addition funnel to 225 mL (13.5 volumes vs. starting material) of $H_2O$ at room temperature over a period of 10 minutes with vigorous stirring. The desired product formed an oil and then precipitated as yellow solids. These solids were stirred at room temperature for an additional 2 hours, collected via vacuum filtration, and dried overnight at 60° C. yielding 14.99 g (86%, 46.1 mmol, 98.5 Area % by HPLC Method A).

Example 2a

Preparation of 4-[(2,4-dinitro-phenyl)-methyl-carbamoyl]-butyric acid methyl ester: The reactor is cleaned and dried then charged with 4-(2,4-dinitro-phenylcarbamoyl)-butyric acid methyl ester, the limiting reagent. The reactor is then inerted and 3 volumes of acetonitrile are charged. Agitation is begun at 100-150 RPM and the batch is heated to 35° C. until solids are dissolved. After cooling to 15 to 25° C., 2.0 equivalents of milled potassium carbonate is added, followed by 1.2 equivalents of dimethyl sulfate. The batch is then agitated at 15 to 25° C. for three hours at which time an additional 0.5 equivalent of milled potassium carbonate is added. Agitation is continued until an in process analysis shows less than 1.0 Area % of starting material remaining (HPLC Method A). Solid potassium carbonate is removed by filtration and the wetcake of base is washed with two volumes of acetonitrile. The same or a second clean dry reactor is charged with 10 volumes of deionized water. The filtrate is then charged to the reactor over 30-90 minutes at 15 to 25° C. Once the transfer is complete the batch is agitated at 15 to 25° C. for 18 to 24 hours to destroy residual dimethyl sulfate. The batch is cooled to 0 to 10° C. over approximately an hour, then isolated by filtration. The wetcake is washed with one volume of deionized water then dried under vacuum at 50° C. to constant weight. Yields are typically 85-95% with purity ranging from 97-99 Area % by HPLC (HPLC Method A).

Example 3

Preparation of 4-[(2,4-Dinitro-phenyl)-methyl-carbamoyl]-butyric acid methyl ester: To a solution of 2,4-dinitroaniline (6.00 g, 32.76 mmol) in acetonitrile (60 mL) was added methyl-5-chloro-5-oxo-valerate (5.44 mL, 39.31 mmol, 1.2 equiv) at 20° C. in one portion. The reaction mixture was then heated to 75° C. Reaction progress was monitored periodically by HPLC (HPLC Method A). The reaction was complete after stirring for 23 hours at 75° C. to give 4-(2,4-dinitro-phenylcarbamoyl)-butyric acid methyl ester. This reaction mixture was cooled to 20° C. and a portion of the solvent was then removed in vacuo to yield a total reaction volume of approximately 25 mL. To the concentrated mixture was then added potassium carbonate (13.58 g, 98.26 mmol, 3.0 equiv) and methyl iodide (10.20 mL, 163.48 mmol, 5.0 equiv.) at 20° C. Reaction progress was monitored periodically by HPLC Method A. The reaction was complete after 17 hours at 20° C. to give 4-[(2,4-dinitro-phenyl)-methyl-carbamoyl]-butyric acid methyl ester. The reaction mixture was filtered to remove excess $K_2CO_3$ and the filtrate was poured into cold water (200 mL) to yield off-white solids. The solid product was collected by vacuum filtration and dried at 60° C. under vacuum/$N_2$ sweep overnight to give 8.914 g, (84% yield) as a light tan solid.

Example 4

Preparation of 4-[(2,4-Dinitro-phenyl)-methyl-carbamoyl]-butyric acid methyl ester: To a stirred suspension of 1-methylamino-2,4-dinitrobenzene (1.00 g, 5.07 mmol) in xylenes (10 mL) was added methyl-5-chloro-5-oxo-valerate (3.50 mL, 25.28 mmol, 5.0 equiv.) at 20° C. The reaction mixture was then heated to reflux, approximately 138° C. Reaction progress was monitored periodically by HPLC Method A. The reaction was complete after stirring for approximately 24 hours at 138° C. The reaction mixture was cooled to 0° C. and hexanes was added (10 mL) to crystallize the product. The resultant slurry was stirred for approximately 1 hour at −10° C. to 0° C. and then filtered. The wet cake was dried at 60° C. under vacuum/$N_2$ sweep overnight to give 1.30 g (79% yield) as an off-while solid.

Example 5

Preparation of 4-(5-Amino-1-methyl-1H-benzoimidazol-2-yl)-butyric acid methyl ester hydrochloride: A one-liter Buchi reactor was charged with 20 grams of 4-[(2,4-dinitro-phenyl)-methyl-carbamoyl]-butyric acid methyl ester, 1.0 g of palladium on carbon (dry basis, 10% Pd), and 180 mL of methanol at ambient temperature. The resulting mixture was subjected to hydrogenation at 40 psi overnight (ca. 18 hours) with a hydrogen mass transfer coefficient (kLa) of 0.12 to 0.28. The reaction mixture was filtered through a thin pad of Celite® 540. To the filtrate was added 2.8 mL of concentrated hydrochloric acid (1.1 eq vs. starting material). The resulting mixture was stirred under reflux for 3.5 hours. Approximately ¾ amount of solvent was removed under reduced pressure.

Then warm tetrahydrofuran (THF) (150 mL) was added while vigorously stirring. The precipitate was collected by filtration and dried overnight under vacuum to afford a coffee-colored solid (16.1 g, yield 92%) with a purity of 98 Area % by HPLC analysis (HPLC Method B). $^1$H NMR (400 MHz, DMSO-d6) δ 7.83 (d, J=8.8 Hz, 1H), 7.50 (s, 1H), 7.27 (d, J=8.6 Hz, 1H), 3.91 (s, 3H), 3.58 (s, 3H), 3.17 (t, J=7.7 Hz, 2H), 2.53 (t, J=7.3 Hz, 2H, overlapped partially with DMSO), 2.07 (quint, J=7.5 Hz, 2H); LC/MS (ESI, m/z) 248 (M+1).

Example 6

Preparation of 4-(5-Amino-1-methyl-1H-benzoimidazol-2-yl)-butyric acid methyl ester hydrochloride: A two liter Buchi reactor was charged with 42.7 g (131.4 mmol, 1.0 equiv.) of 4-[(2,4-dinitro-phenyl)-methyl-carbamoyl]-butyric acid methyl ester, 20 g of 10% palladium on carbon (4.7% weight ratio palladium vs. starting material), and 650 mL of methanol at ambient temperature. The resulting mixture was subjected to hydrogenation at 40 psi overnight, about 18 hours. HPLC indicated that the reaction was complete in about 6-7 hours (HPLC Method B). The reaction mixture was filtered through a thin layer of Celite® 540. To the filtrate was added 11 mL of concentrated hydrochloric acid (1.0 equiv.). The resulting mixture was stirred under reflux for 3.5 hours. Approximately a half amount of solvent was removed under reduced pressure. Tert-butyl methyl ether (MTBE, 900 mL) was added with vigorous stirring. The precipitate was collected by filtration and washed with a mixture of MeOH-MTBE (1:10). The product was dried in an over at 60° C. overnight under vacuum to afford a tan solid (36.8 g, 99% yield) with a purity of 99 Area % by HPLC analysis (HPLC Method B).

Example 6a

Preparation of 4-(5-Amino-1-methyl-1H-benzoimidazol-2-yl) -butyric acid methyl ester hydrochloride: A one liter Buchi reactor was charged with 42.7 g (131.4 mmol, 1.0 equiv.) of 4-[(2,4-dinitro-phenyl)-methyl-carbamoyl]-butyric acid methyl ester, 20 g of 10% palladium on carbon (4.7% weight ratio palladium vs. starting material), and 650 mL of methanol at ambient temperature. The resulting mixture was subjected to hydrogenation at 40 psi overnight, about 18 hours. HPLC indicated that the reaction was complete in about 6-7 hours (HPLC Method B). The reaction mixture was filtered through a thin layer of Celite® 540. To the filtrate was added 12 mL of concentrated hydrochloric acid (1.1 equiv.). The resulting mixture was stirred under reflux for 3.5 hours. Solvent was removed under reduced pressure, and the solids were slurried in 1800 mL of 2 vol % of Methanol/Tert-butyl methyl ether at room temperature overnight. The solids were collected by filtration. The product was dried at 45-50° C. overnight under vacuum to afford a coffee-colored solid (36.8 g, 99% yield) with a purity of 99 Area % by HPLC analysis (HPLC Method B).

Example 7

Preparation of 4-{5-[Bis-(2-chloro-ethyl)-amino]-1-methyl-1H-benzoimidazol-2-yl}-butyric acid methyl ester: A one-liter, three neck, round bottom flask equipped with a stirring bar, condenser with nitrogen sweep, thermocouple with temperature controller, and heating mantle was charged with 4-(5-amino-1-methyl-1H-benzoimidazol -2-yl)-butyric acid methyl ester hydrochloride (15.0 g, 52.9 mmol. 1.0 eq), and chloroacetic acid (105.0 g, 21 eq.), and 22.5 mL of dry tetrahydrofuran (THF). The slurry was stirred in a tap water bath to allow all of the solids to be dissolved. Borane-THF (370.0 mL, 370 mmol, 7 eq.) was added slowly via an addition funnel. When the addition of BH$_3$-THF was completed, the resulting reaction solution was stirred at room temperature for 5 hours and quenched with methanol at room temperature. The resulting solution was concentrated to approximately one-third weight by evaporation and neutralized to pH 7-8 with an aqueous sodium carbonate solution in an ice-water bath. A tan solid was collected by vacuum filtration then washed with water and methyl tert-butyl ether. After drying on the rotary evaporator with house vacuum at room temperature overnight, a tan solid was obtained in an essentially quantitative yield with a purity of 97.8 Area % (HPLC Method C). $^1$H NMR (400 MHz, DMSO-d6) δ 7.32 (d, J=8.8 Hz, 1H), 6.92 (d, J=2.3 Hz, 1H), 6.78 (dd, J=8.8, 2.3 Hz, 1H), 3.70 (br s, 8H), 3.66 (s, 3H), 3.59 (s, 3H), 2.83 (t, J=7.4 Hz, 2H), 2.48 (t, J=7.4 Hz, 2H, overlapped partially with DMSO), 2.01 (quint, J=7.4 Hz, 2H); LC/MS (ESI, m/z) 372 (M+1), mp 60-63° C. dec.

Example 8

Recrystallization of 4-{5-[bis-(2-chloro-ethyl)-amino]-1-methyl-1H-benzoimidazol-2-yl}-butyric acid methyl ester:
To a 500 mL jacked reactor equipped with an air powered overhead stirrer, thermocouple, reflux condenser, and nitrogen blanket were charged 20.0 g (53.7 mmol) of crude 4-{5-[Bis-(2-chloro-ethyl)-amino]-1-methyl-1H-benzoimidazol-2-yl}-butyric acid methyl ester (98.3 HPLC A %) and 400 mL (20 volumes) of MTBE. This stirred mixture was heated to approximately 40° C., at which point 1.00 g (5 wt %) of celite was added. The mixture was then heated to 50° C., where all the solids, except for the celite, dissolved. After stirring at 50° C. for approximately 2 hours, the mixture was filtered at 45° C. in order to remove the celite. The reactor and wetcake were washed with 120 mL (6 volumes) of warm MTBE (45° C.). The combined filtrates were returned to the reactor and 420 mL (21 volumes) of MTBE was removed by vacuum distillation at 45° C. The resultant solution was slowly cooled to 35° C., the cloud point, at which point the batch was seeded with previously recrystallized material. The chiller was then set at 22° C. The batch cooled and precipitated at 33° C. At approximately 30° C., 100 mL (5 volumes) of heptane was added over 9 minutes as an anti-solvent. The batch was then cooled to 0° C. and stirred for 1.5 hours. The solids were collected by vacuum filtration and the wetcake and reactor were washed with 80 mL (4 volumes) of heptane. The recrystallized product was dried overnight in the vacuum oven at 30° C. to yield 14.5 g, 72% of product as a white crystalline solid with a purity of 99.3 Area % by HPLC (HPLC Method C).

Example 9

Preparation of Bendamustine hydrochloride: 4-{5-[Bis-(2-chloro-ethyl) -amino]-1-methyl-1H-benzoimidazol-2-yl}-butyric acid methyl ester (10.0 g) and concentrated hydrochloric acid (40 mL) were heated at reflux for 4 hours. The hydrolysis was driven to completion by evaporating 70 wt % of the solvent in the reaction mixture at 58° C. under reduced pressure. After warm water was added, the resulting mixture was allowed to cool to 0 to 5° C. to precipitate the product. Vacuum filtration and washing by cold water and then cold acetone gave an off-white solid (8.6 g, 81%) with a purity of 99.1 Area % (HPLC Method C). The crude product was further treated by refluxing with charcoal in ethanol, filtering while hot, cooled, the crystals collected by filtration, and washed with hot acetone (2-4 times when needed) to increase the purity. $^1$H NMR (400 MHz, DMSO-d6) δ 12.3 (br s, 1H), 7.72 (d, J=9.3 Hz, 1H), 7.14 (d, J=2.3 Hz, 1H), 6.89 (dd, J=9.3, 2.3 Hz, 1H), 3.90 (s, 3H), 3.80 (m, 8H), 3.14 (t, J=7.6 Hz, 2H), 2.42 (t, J=7.2 Hz, 2H), 2.01 (quint, J=7.6 Hz, 2H); LC/MS (ESI, m/z) 358 (M+1).

Example 10

Purification of Bendamustine hydrochloride (Method 1): Bendamustine HCl (9.2 g) was stirred in a mixture of dimethylformamide (DMF):THF (2:1, 40 mL) at 75° C. for about 30 min., cooled to ambient temperature, and the solids collected by filtration. The collected solids were heated at reflux in acetone for 1 hour and cooled to room temperature. The solids (bendamustine hydrochloride Form 1) were collected by filtration and dried. The X-ray powder diffraction (XRPD) spectrum is shown in FIG. 1. The accompanying data for the first 25 XRPD peaks, is shown below.

First 25 Peaks from XRPD Spectrum of Bendamustine Hydrochloride Purified via Method 1

| Pos. [°2 Th.] | Height [cts] | FWHM [°2 Th.] | d-spacing [Å] | Rel. Int. [%] |
|---|---|---|---|---|
| 7.6249 | 129.23 | 0.1152 | 11.58504 | 2.72 |
| 8.4141 | 820.97 | 0.0576 | 10.50017 | 17.29 |
| 8.7693 | 134.64 | 0.0576 | 10.07556 | 2.83 |
| 13.4737 | 297.13 | 0.0768 | 6.56639 | 6.26 |
| 14.0691 | 3477.32 | 0.0864 | 6.28979 | 73.22 |
| 14.6989 | 119.85 | 0.2304 | 6.02170 | 2.52 |
| 15.4126 | 162.93 | 0.1152 | 5.74442 | 3.43 |
| 16.3793 | 173.92 | 0.0768 | 5.40751 | 3.66 |
| 16.8362 | 1115.50 | 0.0480 | 5.26177 | 23.49 |
| 16.8821 | 936.85 | 0.0384 | 5.24756 | 19.73 |
| 17.5026 | 2179.32 | 0.0864 | 5.06291 | 45.89 |
| 18.4203 | 864.84 | 0.0864 | 4.81268 | 18.21 |
| 20.9310 | 1195.40 | 0.0864 | 4.24073 | 25.17 |
| 21.5473 | 1371.51 | 0.0864 | 4.12079 | 28.88 |
| 21.7095 | 467.20 | 0.0576 | 4.09038 | 9.84 |
| 22.0041 | 4570.52 | 0.0864 | 4.03627 | 96.23 |
| 22.2546 | 1038.40 | 0.0864 | 3.99140 | 21.86 |
| 22.9040 | 4451.30 | 0.1056 | 3.87968 | 93.72 |
| 23.2373 | 254.63 | 0.0768 | 3.82479 | 5.36 |
| 23.3957 | 409.22 | 0.0672 | 3.79924 | 8.62 |
| 23.7027 | 1352.63 | 0.0864 | 3.75073 | 28.48 |
| 24.1049 | 77.19 | 0.2304 | 3.68905 | 1.63 |
| 24.8599 | 2491.32 | 0.0768 | 3.57869 | 52.46 |
| 25.1653 | 4749.39 | 0.0768 | 3.53595 | 100.00 |
| 25.3512 | 1328.24 | 0.0576 | 3.51045 | 27.97 |

*The use of ZBG plates typically introduces a Positive sample height displacement and results in small (0.05° to 0.2°) offset in 2θ values. If fewer than 25 peaks are found all are reported.

Example 11

Figure 2:
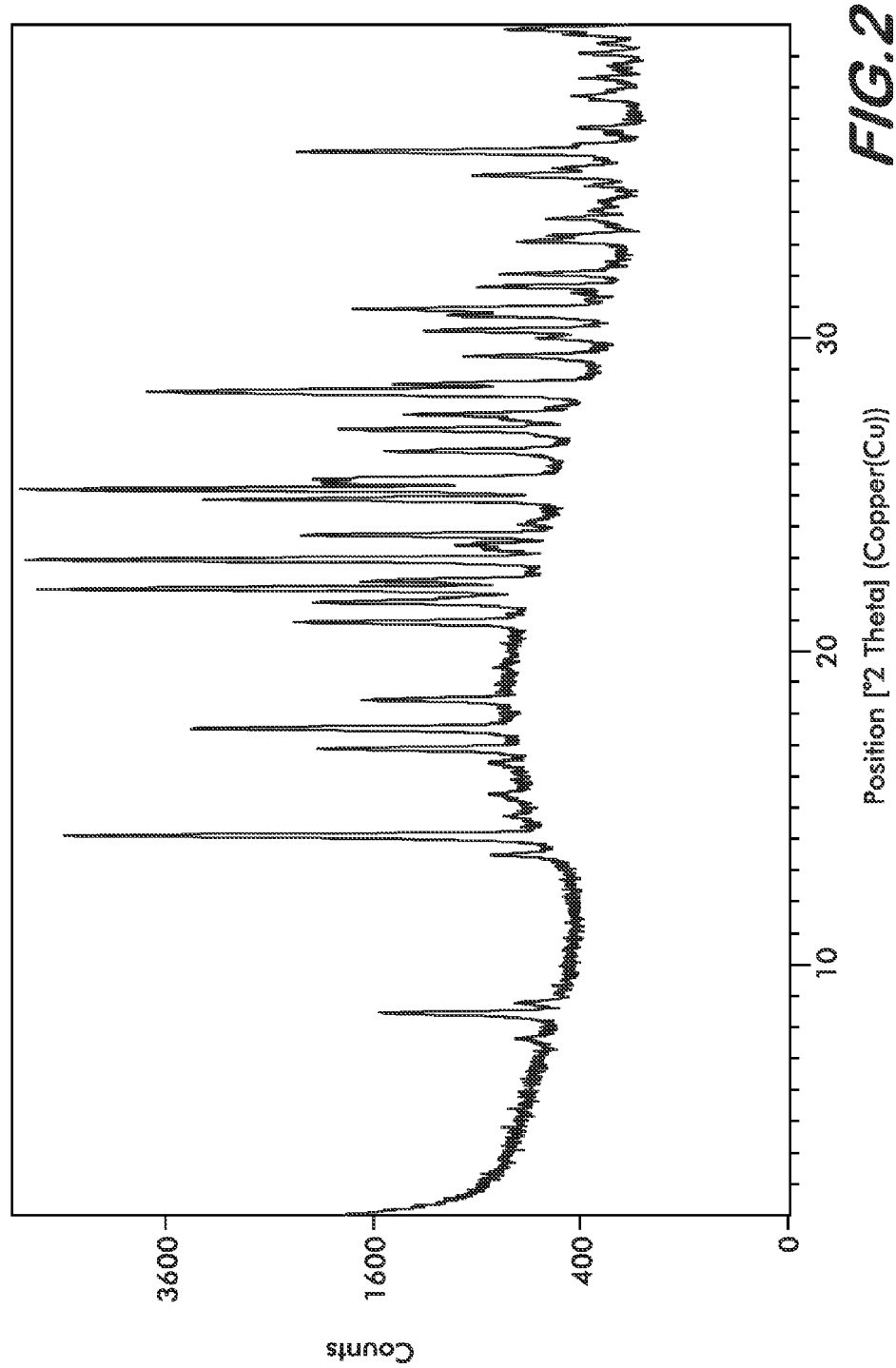
FIG. 2 is an XRPD spectrum of bendamustine hydrochloride purified by Method 2 described herein.

Purification of Bendamustine hydrochloride (Method 2): Bendamustine HCl (9.2 g) was stirred in a mixture of DMF:THF (2:1, 40 mL) at 75° C. for about 30 min., cooled to ambient temperature, and the solids collected by filtration. The collected solids were stirred in acetone at ambient temperature for about 1 hour. The solids (bendamustine hydrochloride Form 1) were collected by filtration and dried. The X-ray powder diffraction (XRPD) spectrum is shown in FIG. 2. The accompanying data for the first 25 XRPD peaks is shown below.

First 25 Peaks from XRPD Spectrum of Bendamustine Hydrochloride Purified via Method 2

| Pos. [°2 Th.] | Height [cts] | FWHM [°2 Th.] | d-spacing [Å] | Rel. Int. [%] |
|---|---|---|---|---|
| 7.6433 | 138.65 | 0.1152 | 11.55714 | 2.72 |
| 8.4102 | 815.45 | 0.0672 | 10.50494 | 15.97 |
| 8.4850 | 981.27 | 0.0576 | 10.41252 | 19.22 |
| 8.7918 | 189.25 | 0.1536 | 10.04983 | 3.71 |
| 13.4995 | 319.12 | 0.1152 | 6.55387 | 6.25 |
| 14.0949 | 4237.65 | 0.0960 | 6.27837 | 83.00 |
| 14.1531 | 3074.36 | 0.0384 | 6.25268 | 60.22 |
| 14.7293 | 140.71 | 0.1152 | 6.00932 | 2.76 |
| 15.4678 | 163.29 | 0.1152 | 5.72405 | 3.20 |
| 16.4221 | 142.70 | 0.1536 | 5.39350 | 2.80 |
| 16.8610 | 1312.60 | 0.0480 | 5.25408 | 25.71 |
| 16.9208 | 1120.27 | 0.0384 | 5.23564 | 21.94 |
| 17.5092 | 2581.60 | 0.1056 | 5.06102 | 50.56 |
| 18.4268 | 970.35 | 0.0672 | 4.81100 | 19.01 |
| 18.5133 | 432.46 | 0.0768 | 4.78871 | 8.47 |
| 20.9241 | 1516.93 | 0.0864 | 4.24211 | 29.71 |
| 21.5606 | 1440.06 | 0.0672 | 4.11829 | 28.21 |
| 21.9947 | 4535.03 | 0.0768 | 4.03798 | 88.83 |
| 22.0757 | 2589.18 | 0.0384 | 4.02335 | 50.71 |
| 22.2366 | 1056.71 | 0.0576 | 3.99459 | 20.70 |
| 22.9359 | 4718.54 | 0.1056 | 3.87436 | 92.42 |
| 23.2484 | 260.37 | 0.0768 | 3.82298 | 5.10 |
| 23.3920 | 444.77 | 0.0768 | 3.79984 | 8.71 |
| 23.7223 | 1650.33 | 0.0768 | 3.74768 | 32.32 |
| 23.7768 | 1096.74 | 0.0576 | 3.73921 | 21.48 |

*The use of ZBG plates typically introduces a positive sample height displacement and results in small (0.05° to 0.2°) offset in 2θ values. If fewer than 25 peaks are found all are reported.

Example 12

Figure 3:
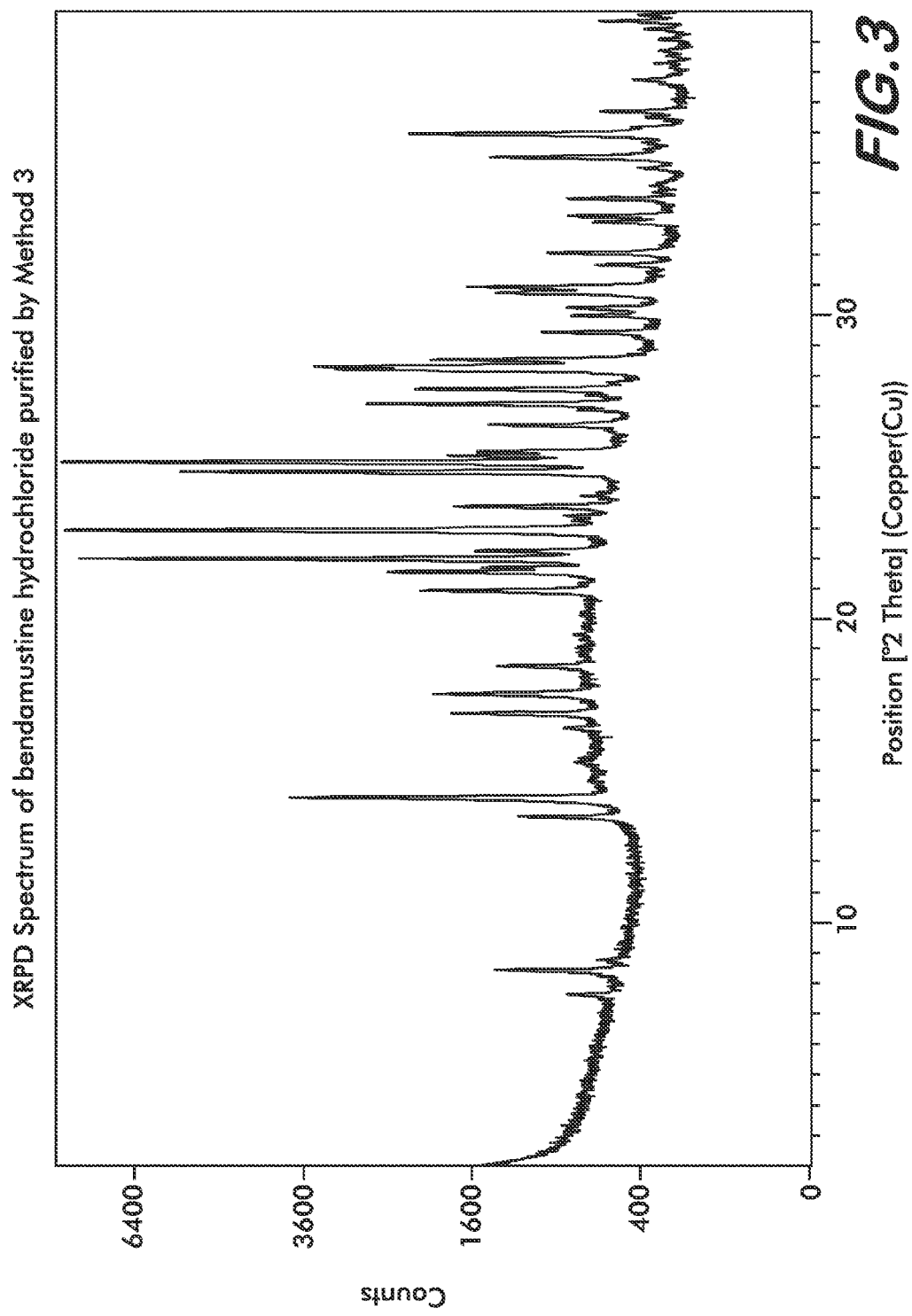
FIG. 3 is an XRPD spectrum of bendamustine hydrochloride purified by Method 3 described herein.

Purification of Bendamustine hydrochloride (Method 3): Bendamustine HCl (3.0 g) was stirred in THF (15 mL) at reflux for about 90 min. and cooled to ambient temperature. The solids (bendamustine hydrochloride Form 1) were collected by filtration and dried. The X-ray powder diffraction (XRPD) spectrum is shown in FIG. 3. The accompanying data for the first 25 XRPD peaks is shown below.

First 25 Peaks from XRPD Spectrum of Bendamustine Hydrochloride Purified via Method 3

| Pos. [°2 Th.] | Height [cts] | FWHM [°2 Th.] | d-spacing [Å] | Rel. Int. [%] |
|---|---|---|---|---|
| 2.0320 | 503.82 | 0.1152 | 43.44109 | 7.01 |
| 7.6433 | 280.48 | 0.0768 | 11.55716 | 3.90 |
| 8.4496 | 849.49 | 0.0576 | 10.45609 | 11.82 |
| 8.7646 | 83.19 | 0.1152 | 10.08104 | 1.16 |
| 13.4988 | 693.12 | 0.0384 | 6.55425 | 9.64 |
| 14.1149 | 3196.51 | 0.1056 | 6.26949 | 44.47 |
| 15.3096 | 100.55 | 0.3072 | 5.78282 | 1.40 |
| 16.3940 | 196.99 | 0.0768 | 5.40269 | 2.74 |
| 16.8838 | 1104.14 | 0.0768 | 5.24703 | 15.36 |
| 17.5065 | 1315.96 | 0.0864 | 5.06180 | 18.31 |
| 18.4340 | 638.95 | 0.0672 | 4.80913 | 8.89 |
| 20.9584 | 1450.75 | 0.0864 | 4.23599 | 20.18 |
| 21.5661 | 1873.73 | 0.0864 | 4.11724 | 26.07 |
| 21.7177 | 800.32 | 0.0768 | 4.08884 | 11.13 |
| 22.0097 | 6722.69 | 0.0864 | 4.03525 | 93.52 |
| 22.2540 | 930.40 | 0.0576 | 3.99150 | 12.94 |
| 22.9532 | 7107.09 | 0.1056 | 3.87148 | 98.87 |
| 23.4138 | 250.57 | 0.0768 | 3.79634 | 3.49 |
| 23.7263 | 1171.50 | 0.0960 | 3.74704 | 16.30 |
| 24.0414 | 154.55 | 0.1536 | 3.69865 | 2.15 |
| 24.8588 | 4966.96 | 0.0768 | 3.57886 | 69.10 |

First 25 Peaks from XRPD Spectrum of Bendamustine Hydrochloride Purified via Method 3

| Pos. [°2 Th.] | Height [cts] | FWHM [°2 Th.] | d-spacing [Å] | Rel. Int. [%] |
|---|---|---|---|---|
| 25.1826 | 7188.16 | 0.0768 | 3.53356 | 100.00 |
| 25.3822 | 1334.49 | 0.0864 | 3.50622 | 18.57 |
| 25.5232 | 1048.88 | 0.0864 | 3.48717 | 14.59 |
| 26.3986 | 978.33 | 0.0768 | 3.37349 | 13.61 |

*The use of ZBG plates typically introduces a positive sample height displacement and results in small (0.05° to 0.2°) offset in 2θ values. If fewer than 25 peaks are found all are reported.

Example 13

Figure 4:
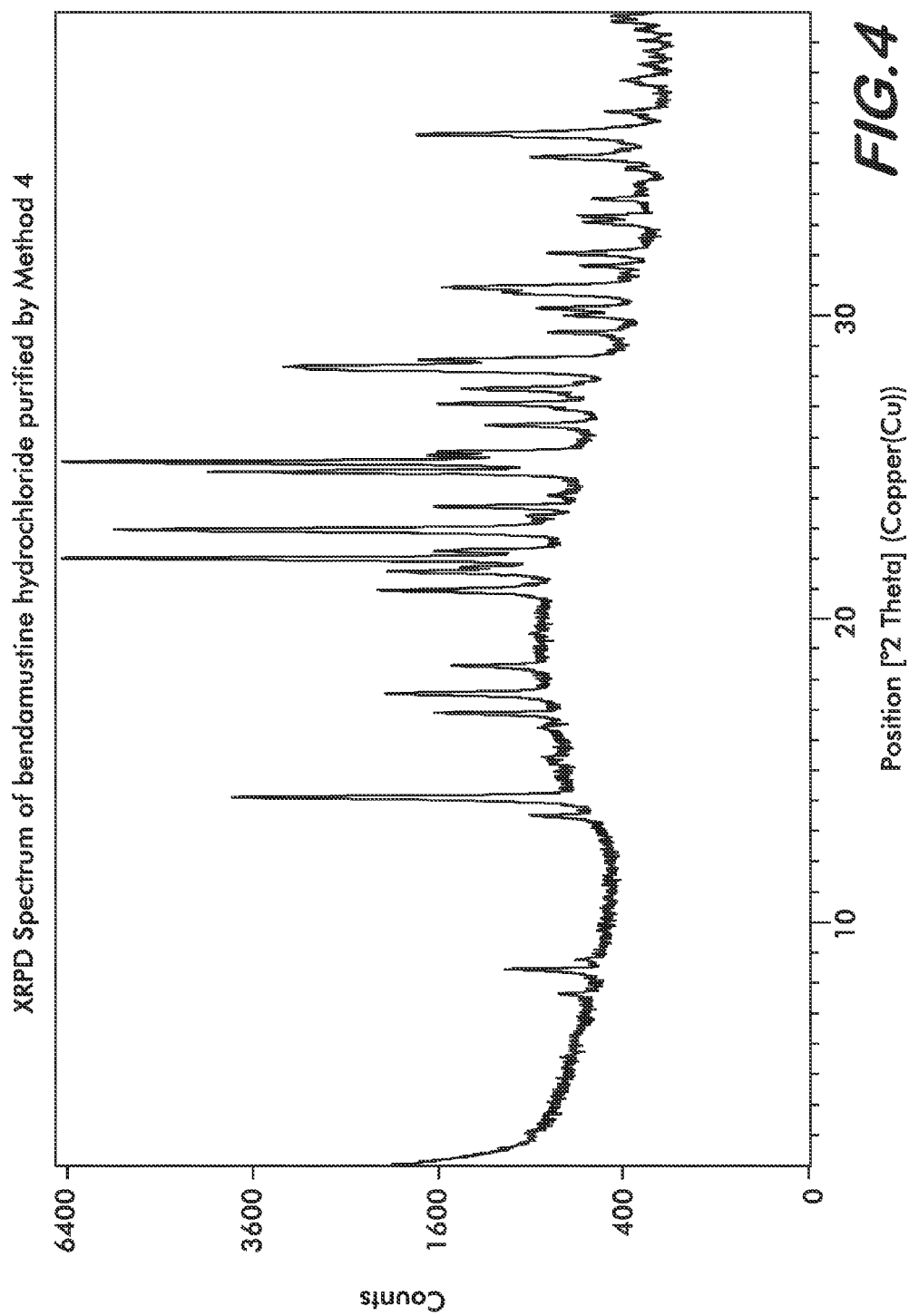
FIG. 4 is an XRPD spectrum of bendamustine hydrochloride purified by Method 4 described herein.

Purification of Bendamustine hydrochloride (Method 4): Bendamustine HCl (0.52 g) was stirred in a mixture of DMF:THF (3:7, 2.6 mL) at ambient temperature for about 1 hour. The solids (bendamustine hydrochloride Form 1) were collected by filtration and dried. The X-ray powder diffraction (XRPD) spectrum is shown in FIG. 4. The accompanying data for the first 25 XRPD peaks is shown below.

First 25 Peaks from XRPD Spectrum of Bendamustine Hydrochloride Purified via Method 4

| Pos. [°2 Th.] | Height [cts] | FWHM [°2 Th.] | d-spacing [Å] | Rel. Int. [%] |
|---|---|---|---|---|
| 7.6575 | 164.93 | 0.0960 | 11.53582 | 2.81 |
| 8.4811 | 444.28 | 0.0672 | 10.41738 | 7.56 |
| 8.7818 | 102.65 | 0.1152 | 10.06133 | 1.75 |
| 13.5143 | 344.59 | 0.0480 | 6.54673 | 5.86 |
| 14.1164 | 3253.28 | 0.1056 | 6.26883 | 55.35 |
| 15.3416 | 62.07 | 0.3072 | 5.77084 | 1.06 |
| 16.3991 | 96.07 | 0.1152 | 5.40103 | 1.63 |
| 16.8933 | 888.25 | 0.0672 | 5.24409 | 15.11 |
| 17.5203 | 1325.05 | 0.0672 | 5.05783 | 22.54 |
| 18.4429 | 654.42 | 0.0864 | 4.80684 | 11.13 |
| 20.9709 | 1400.85 | 0.0384 | 4.23274 | 23.83 |
| 21.5705 | 1291.73 | 0.0768 | 4.11642 | 21.98 |
| 21.7261 | 641.24 | 0.0480 | 4.08730 | 10.91 |
| 22.0284 | 5600.37 | 0.1056 | 4.03187 | 95.28 |
| 22.2861 | 806.88 | 0.0864 | 3.98583 | 13.73 |
| 22.9610 | 4900.64 | 0.1248 | 3.87018 | 83.38 |
| 23.4123 | 258.41 | 0.0960 | 3.79658 | 4.40 |
| 23.7252 | 989.03 | 0.0960 | 3.74722 | 16.83 |
| 24.0710 | 121.20 | 0.1152 | 3.69417 | 2.06 |
| 24.8736 | 3513.92 | 0.1056 | 3.57675 | 59.79 |
| 25.1970 | 5877.55 | 0.1152 | 3.53167 | 100.00 |
| 25.4070 | 1129.75 | 0.0576 | 3.50286 | 19.22 |
| 25.5255 | 1008.55 | 0.0960 | 3.48687 | 17.16 |
| 26.3940 | 670.34 | 0.0864 | 3.37407 | 11.41 |
| 27.1208 | 1105.35 | 0.0960 | 3.28528 | 18.81 |

*The use of ZBG plates typically introduces a positive sample height displacement and results in small (0.05° to 0.2°) offset in 2θ values. If fewer than 25 peaks are found all are reported.

Example 14

Purification of Bendamustine hydrochloride (Method 5): Bendamustine HCl (0.52 g) was stirred in a mixture of DMF:THF (1:9, 2.6 mL) at ambient temperature for about 2 hours. The solids (bendamustine hydrochloride Form 1) were collected by filtration and dried. The X-ray powder diffraction (XRPD) spectrum is shown in FIG. 5. The accompanying data for the first 25 XRPD peaks is shown below.

First 25 Peaks from XRPD Spectrum of Bendamustine Hydrochloride Purified via Method 5

| Pos. [°2 Th.] | Height [cts] | FWHM [°2 Th.] | d-spacing [Å] | Rel. Int. [%] |
|---|---|---|---|---|
| 7.6654 | 202.84 | 0.0768 | 11.52388 | 2.41 |
| 8.4815 | 453.90 | 0.0768 | 10.41686 | 5.40 |
| 8.7904 | 87.16 | 0.1536 | 10.05143 | 1.04 |
| 10.6465 | 72.72 | 0.1152 | 8.30291 | 0.86 |
| 13.5244 | 345.28 | 0.0672 | 6.54186 | 4.10 |
| 14.1344 | 3774.64 | 0.1056 | 6.26092 | 44.87 |
| 15.3403 | 88.02 | 0.2304 | 5.77133 | 1.05 |
| 16.4171 | 189.20 | 0.0960 | 5.39512 | 2.25 |
| 16.9015 | 784.38 | 0.0672 | 5.24160 | 9.32 |
| 17.5225 | 1400.31 | 0.1056 | 5.05719 | 16.64 |
| 18.4505 | 851.05 | 0.1056 | 4.80486 | 10.12 |
| 18.7383 | 449.51 | 0.0768 | 4.73172 | 5.34 |
| 20.9733 | 1626.52 | 0.0960 | 4.23227 | 19.33 |
| 21.5866 | 1723.65 | 0.1056 | 4.11339 | 20.49 |
| 21.7397 | 889.51 | 0.0864 | 4.08476 | 10.57 |
| 22.0320 | 8226.43 | 0.1056 | 4.03122 | 97.78 |
| 22.2817 | 1258.91 | 0.0768 | 3.98661 | 14.96 |
| 22.9772 | 5368.53 | 0.1152 | 3.86750 | 63.81 |
| 23.4184 | 311.09 | 0.0960 | 3.79562 | 3.70 |
| 23.7493 | 1025.61 | 0.1056 | 3.74347 | 12.19 |
| 24.0827 | 170.13 | 0.1152 | 3.69239 | 2.02 |
| 24.8908 | 4534.54 | 0.1056 | 3.57432 | 53.90 |
| 25.1998 | 8413.27 | 0.1056 | 3.53119 | 100.00 |
| 25.4138 | 1058.05 | 0.0672 | 3.50194 | 12.58 |
| 25.5352 | 1245.64 | 0.0768 | 3.48556 | 14.81 |

*The use of ZBG plates typically introduces a positive sample height displacement and results in small (0.05° to 0.2°) offset in 2θ values. If fewer than 25 peaks are found all are reported.

X-Ray Powder Diffraction Methods: Powder XRD patterns were recorded on a PANalytical X'Pert Pro diffractometer equipped with an X'celerator detector using Cu Kα radiation at 40 kV and 40 mA. Kα1 radiation was obtained with a highly oriented crystal (Ge111) incident bean monochromator. A 10 mm beam mask and fixed (¼°) divergence and anti-scatter (⅛°) slits were inserted on the incident beam side. A fixed 0.10 mm receiving slit was inserted on the diffracted beam side. The X-ray powder pattern scan was collected from ca. 2 to 40° 2θ with a 0.0080° step size and 96.06 sec counting time which resulted in a scan rate of approximately 0.5°/min.

The sample was spread on a silicon zero background (ZBG) plate for measurement. The sample was rotated at 4°/min on a PANalytical PW2064 Spinner.

Measurement of the Si reference standard before the data collection resulted in values for 2θ and intensity that were well within the tolerances of 28.38<2θ<28.50 and significantly greater than the minimum peak height of 150 cps.

Bendamustine hydrochloride produced by the methods described herein resulted in a crystalline form of bendamustine hydrochloride that is the Form 1 polymorph. This polymorph may be characterized by one, two, three, four, five, or more reflection peaks that are characteristic of Form 1, as well as by reference to the XRPD spectra provided herein.

As those skilled in the art will appreciate, numerous modifications and variations of the present invention are possible in light of the above teachings. It is therefore understood that within the scope of the appended claims, the invention may be practiced otherwise than as specifically described herein, and the scope of the invention is intended to encompass all such variations.

What is claimed:

1. A process for the preparation of a compound of formula I:

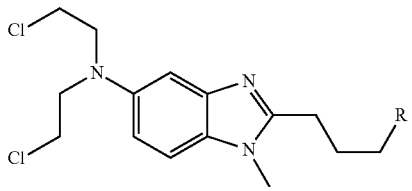

or a pharmaceutically acceptable salt thereof, wherein R is a masked carboxylic acid, comprising:
reductively alkylating with chloroacetic acid or chloroacetaldehyde, a compound of formula II:

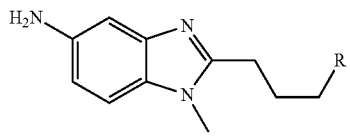

or a pharmaceutically acceptable salt thereof.

2. The process of claim 1, wherein the step of reductively alkylating a compound of formula II is performed in the presence a reducing agent, for a time and under conditions sufficient to produce the compound of formula I.

3. The process of claim 2, wherein the reducing agent is borane, sodium cyanoborohydride, sodium triacetoxyborohydride, or sodium borohydride.

4. The process of claim 2, wherein the reducing agent is hydrogen.

5. The process of claim 2, wherein the reducing agent is ammonium carbonate.

6. The process of claim 1, wherein R is —C(=O)OCH$_3$ or —C(=O)OCH$_2$CH$_3$.

7. The process of claim 1, wherein the compound of formula II

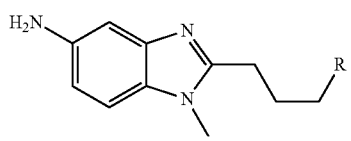

or the pharmaceutically acceptable salt thereof, is prepared by a process comprising: reducing a compound of formula III

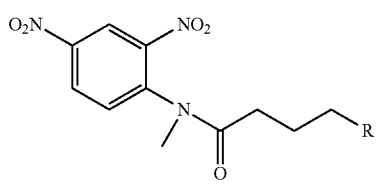

for a time and under conditions sufficient to reduce the nitro groups and form a compound of formula IV:

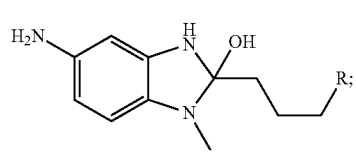

dehydrating the compound of formula IV for a time and under conditions sufficient to produce the compound of formula II; and
optionally isolating the compound of formula II.

8. The process of claim 7, wherein R is —C(=O)OCH$_3$ or —C(=O)OCH$_2$CH$_3$.

9. The process of claim 7, wherein said reducing of a compound of formula III is carried out by catalytic hydrogenation.

10. The process of claim 7, wherein said reducing of a compound of formula III is carried out in the presence of sodium dithionite.

11. The process of claim 7, wherein dehydrating is carried out in the presence of acid.

12. The process of claim 7, wherein the dehydrating is carried out in the presence of base.

13. The process of claim 7, wherein the compound of formula III is prepared by a process comprising contacting 2,4-dinitroaniline:

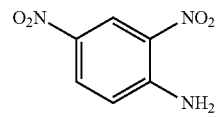

with a compound of formula V

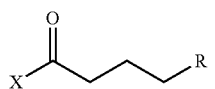

wherein X is Cl, Br, or I;
for a time and under conditions sufficient to produce the compound of formula VI:

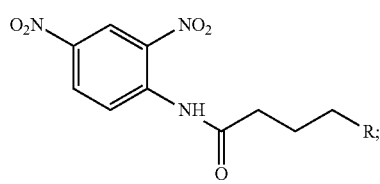

optionally isolating the compound of formula VI;
methylating the compound of formula VI for a time and under conditions sufficient to produce the compound of formula III.

14. The process of claim 13, wherein X is Cl.

15. The process of claim 13, wherein R is —C(=O)OCH$_3$ or —C(=O)OCH$_2$CH$_3$.

16. The process of claim 13, wherein the compound of formula VI is produced in the presence of base.

17. The process of claim 13, wherein the step of methylating the compound of formula VI comprises contacting the compound of formula VI with a methylating agent and an inorganic base.

18. The process of claim 13, wherein the compound of formula VI is isolated by filtration.

19. The process of claim 13, further comprising isolating the compound of formula III.

20. The process of claim 19, wherein the compound of formula III is isolated by precipitating the compound of formula III from an aqueous solution and filtering to obtain the compound of formula III.

21. The process of claim 7, wherein the compound of formula III is prepared by a process comprising reacting 2,4-dinitroaniline:

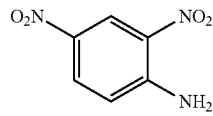 [SMILES: Nc1ccc([N+](=O)[O-])cc1[N+](=O)[O-]]

with a compound of formula V

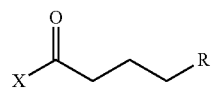

wherein X is OH;
for a time and under conditions sufficient to produce the compound of formula VI:

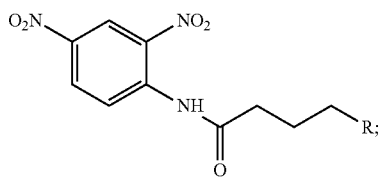

optionally isolating the compound of formula VI; and
methylating the compound of formula VI for a time and under conditions sufficient to produce the compound of formula III.

22. The process of claim 21, wherein the process is carried out in the presence of a coupling agent and optionally, a catalyst.

23. The process of claim 7, wherein the compound of formula III is prepared by a process comprising contacting 1-methylamino-2,4-dinitrobenzene:

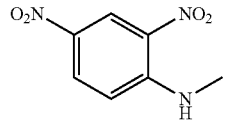

with a compound of formula V

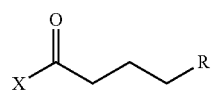

wherein X is Cl, Br, or I; for a time and under conditions sufficient to produce the compound of formula III.

24. The process of claim 23, wherein X is Cl.

25. The process of claim 23, wherein R is —C(═O)OCH₃ or —C(═O)OCH₂CH₃.

26. A process for the preparation of bendamustine, or a pharmaceutically acceptable salt thereof:

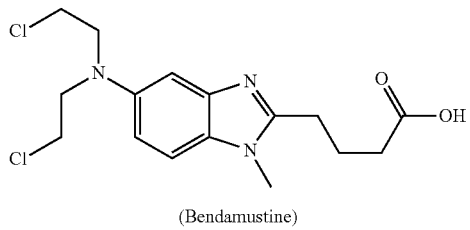 [SMILES: Cn1c(CCCC(=O)O)nc2cc(N(CCCl)CCCl)ccc21]

(Bendamustine)

comprising treating a compound of formula I:

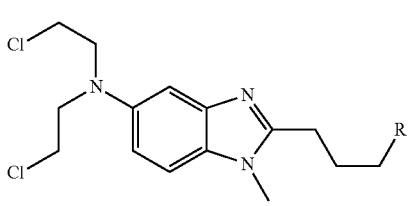

or a pharmaceutically acceptable salt thereof, wherein
R is —C(═O)SC₁₋₆alkyl, -oxazole, —CN, —C(═O)NH₂, —C(═O)NH(C₁₋₆alkyl), —C(═O)N(C₁₋₆alkyl)₂, —CH₂OH, -phenyl, —CH₂OC₁₋₆alkyl, or —C(OC₁₋₆alkyl)₃;
for a time and under conditions sufficient to form bendamustine, or a pharmaceutically acceptable salt thereof;
isolating the bendamustine or the pharmaceutically acceptable salt thereof; and
optionally purifying the bendamustine, or the pharmaceutically acceptable salt thereof.

27. The process of claim 26, wherein the compound of formula I is treated with acid.

28. The process of claim 27, wherein the acid is concentrated hydrochloric acid and the pharmaceutically acceptable salt of bendamustine is bendamustine hydrochloride.

29. The process of claim 26, wherein the pharmaceutically acceptable salt of bendamustine is isolated by filtration.

30. The process of claim 26, wherein the step of purifying the bendamustine comprises heating the pharmaceutically acceptable salt of bendamustine with charcoal in a C₁₋₆alkyl alcohol.

31. The process of claim 30, further comprising treatment of the pharmaceutically acceptable salt of bendamustine with acetone.

32. A process for preparing bendamustine, or a pharmaceutically acceptable salt thereof, comprising:
contacting 1-methylamino-2,4-dinitrobenzene:

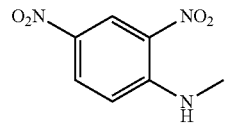

with a compound of formula V:

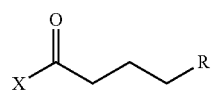

wherein X is Cl, Br, or I and R is a masked carboxylic acid;
for a time and under conditions sufficient to produce a compound of formula III:

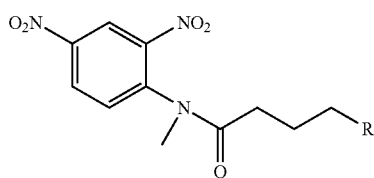

reducing the compound of formula III for a time and under conditions sufficient to reduce the nitro groups and form a compound of formula IV:

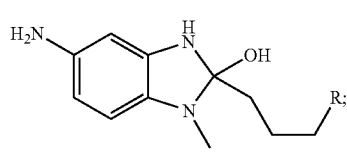

dehydrating the compound of formula IV for a time and under conditions sufficient to produce a compound of formula II:

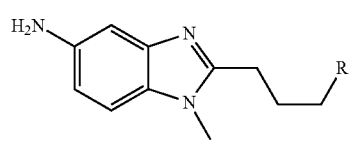

optionally isolating the compound of formula II;

reductively alkylating the compound of formula II with chloroacetic acid or chloroacetaldehyde to produce a compound of formula I:

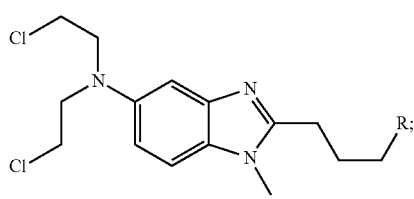

treating the compound of formula I for a time and under conditions sufficient to form bendamustine, or a pharmaceutically acceptable salt thereof;

isolating the bendamustine or the pharmaceutically acceptable salt thereof and optionally purifying the bendamustine, or the pharmaceutically acceptable salt thereof 33. A process for preparing bendamustine, or a pharmaceutically acceptable salt thereof, comprising:

contacting 2,4-dinitroaniline:

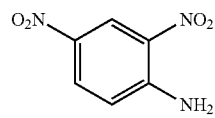

with a compound of formula V:

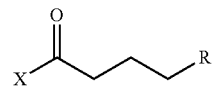

wherein X is Cl, Br, or I and R is a masked carboxylic acid;

for a time and under conditions sufficient to produce the compound of formula VI:

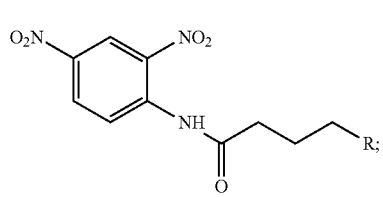

optionally isolating the compound of formula VI;

methylating the compound of formula VI for a time and under conditions sufficient to produce a compound of formula III:

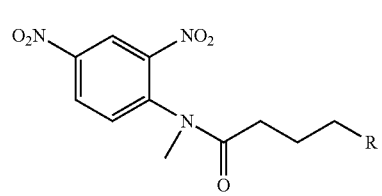

reducing the compound of formula III for a time and under conditions sufficient to reduce the nitro groups and form a compound of formula IV:

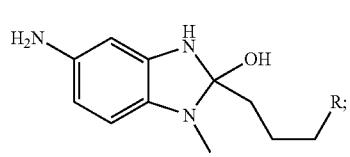

dehydrating the compound of formula IV for a time and under conditions sufficient to produce a compound of formula II:

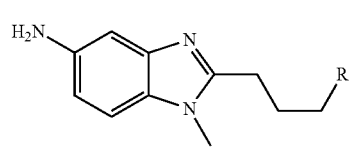

optionally isolating the compound of formula II;

reductively alkylating the compound of formula II with chloroacetic acid or chloroacetaldehyde to produce a compound of formula I:

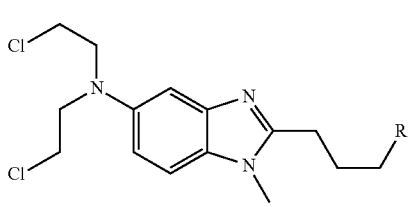
I treating the compound of formula I, for a time and under conditions sufficient to form bendamustine, or a pharmaceutically acceptable salt thereof;
isolating the bendamustine or the pharmaceutically acceptable salt thereof and
optionally purifying the bendamustine, or the pharmaceutically acceptable salt thereof 34. A process for preparing bendamustine, or a pharmaceutically acceptable salt thereof, comprising:
contacting 2,4-dinitroaniline:

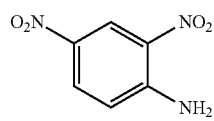

with a compound of formula V:

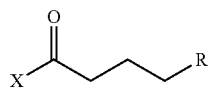
V wherein X is Cl, Br, or I and R is —C(=O)OC$_{1-6}$alkyl, —C(=O)Ophenyl, —C(=O)SC$_{1-6}$alkyl, -oxazole, —CN, —C(=O)NH(C$_{1-6}$alkyl), —C(=O)N(C$_{1-6}$alkyl)$_2$ or —C(OC$_{1-6}$alkyl)$_3$;
for a time and under conditions sufficient to produce the compound of formula VI:

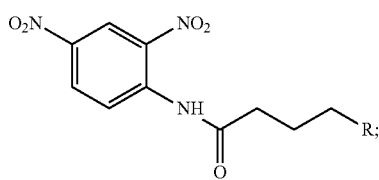
VI optionally isolating the compound of formula VI;
methylating the compound of formula VI for a time and under conditions sufficient to produce a compound of formula III:

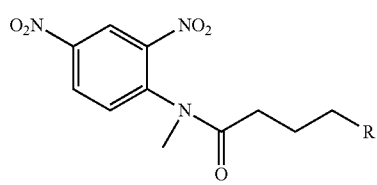
III reducing the compound of formula III for a time and under conditions sufficient to reduce the nitro groups and form a compound of formula IV:

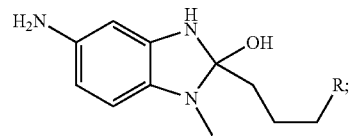
IV dehydrating the compound of formula IV for a time and under conditions sufficient to produce a compound of formula II:

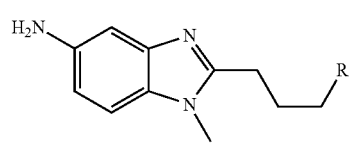
II optionally isolating the compound of formula II;
reductively alkylating the compound of formula II with chloroacetic acid or chloroacetaldehyde to produce a compound of formula I:

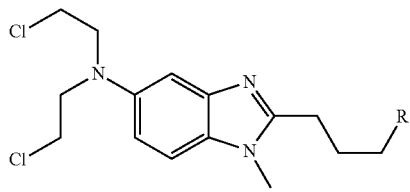
I hydrolyzing the compound of formula I, for a time and under conditions sufficient to form bendamustine, or a pharmaceutically acceptable salt thereof;
isolating the bendamustine or the pharmaceutically acceptable salt thereof; and
optionally purifying the bendamustine, or the pharmaceutically acceptable salt thereof.

35. A process for preparing bendamustine, or a pharmaceutically acceptable salt thereof, comprising
contacting 2,4-dinitroaniline:

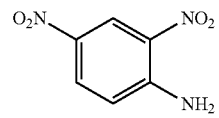

with a compound of formula V:

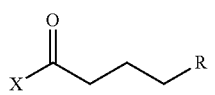
V wherein X is OH and R is —C(=O)OC$_{1-6}$alkyl, —C(=O)Ophenyl, —C(=O)SC$_{1-6}$alkyl, -oxazole, —CN, —C(=O)NH(C$_{1-6}$alkyl), —C(=O)N(C$_{1-6}$alkyl)$_2$ or —C(OC$_{1-6}$alkyl)$_3$;
for a time and under conditions sufficient to produce a compound of formula VI:

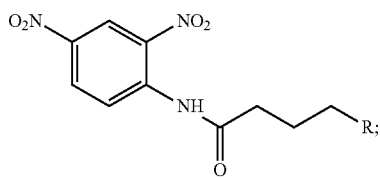

optionally isolating the compound of formula VI;
methylating the compound of formula VI for a time and under conditions sufficient to produce a compound of formula III:

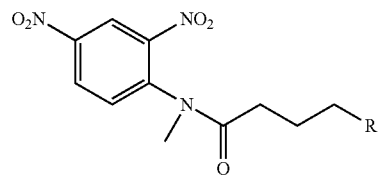

reducing the compound of formula III for a time and under conditions sufficient to reduce the nitro groups and form a compound of formula IV:

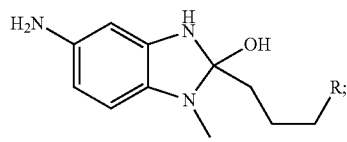

dehydrating the compound of formula IV for a time and under conditions sufficient to produce a compound of formula II:

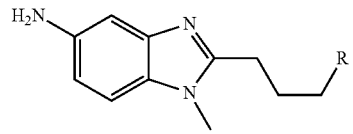

optionally isolating the compound of formula II;
reductively alkylating the compound of formula II with chloroacetic acid or chloroacetaldehyde to produce a compound of formula I:

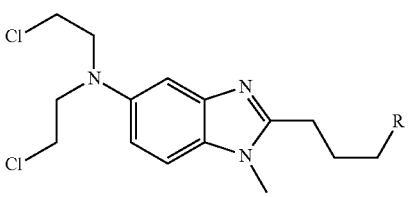

treating the compound of formula I, for a time and under conditions sufficient to form bendamustine, or a pharmaceutically acceptable salt thereof;
isolating bendamustine or the pharmaceutically acceptable salt thereof; and
optionally purifying bendamustine, or the pharmaceutically acceptable salt thereof.

* * * * *